US 6,604,404 B2

(12) United States Patent
Paltieli et al.

(10) Patent No.: US 6,604,404 B2
(45) Date of Patent: Aug. 12, 2003

(54) CALIBRATION METHOD AND APPARATUS FOR CALIBRATING POSITION SENSORS ON SCANNING TRANSDUCERS

(75) Inventors: Yoav Paltieli, Haifa (IL); Ron Nagar, Haifa (IL); David Taran, Tel Aviv (IL)

(73) Assignee: Ultraguide Ltd., Yokneam (IL)

( * ) Notice: Subject to any disclaimer, the term of this patent is extended or adjusted under 35 U.S.C. 154(b) by 0 days.

(21) Appl. No.: 09/950,644

(22) Filed: Sep. 13, 2001

(65) Prior Publication Data

US 2002/0035864 A1 Mar. 28, 2002

Related U.S. Application Data

(62) Division of application No. 09/566,948, filed on May 8, 2000, now Pat. No. 6,311,540, which is a division of application No. 09/222,950, filed on Dec. 30, 1998, now Pat. No. 6,138,495.

(30) Foreign Application Priority Data

Dec. 31, 1997 (IL) .................................................. 122839

(51) Int. Cl.⁷ ............................................. G01N 29/00
(52) U.S. Cl. ....................................................... 73/1.82
(58) Field of Search ................................ 73/1.75, 1.79, 73/1.82, 1.86; 378/207; 324/202

(56) References Cited

U.S. PATENT DOCUMENTS

| | | | | |
|---|---|---|---|---|
| 4,407,294 A | * | 10/1983 | Vilkomerson | 600/461 |
| 4,426,726 A | * | 1/1984 | Cheetham | 378/206 |
| 4,567,896 A | | 2/1986 | Barnea et al. | |
| 4,671,292 A | * | 6/1987 | Matzuk | 600/445 |
| 4,794,931 A | * | 1/1989 | Yock | 600/439 |
| 4,896,673 A | | 1/1990 | Rose et al. | |
| 5,538,004 A | * | 7/1996 | Bamber | 128/916 |
| 5,574,212 A | * | 11/1996 | Madsen et al. | 73/1.82 |
| 5,647,373 A | * | 7/1997 | Paltieli | 600/461 |
| 5,891,034 A | * | 4/1999 | Bucholz | 600/426 |
| 5,891,495 A | * | 4/1999 | Cain et al. | 426/101 |
| 6,138,495 A | * | 10/2000 | Paltieli et al. | 73/1.86 |
| 6,311,540 B1 | * | 11/2001 | Paltieli et al. | 73/1.82 |

FOREIGN PATENT DOCUMENTS

| | | |
|---|---|---|
| DE | 296 19 823 | 3/1997 |
| EP | 0 654 244 | 5/1995 |
| EP | 0 736 284 | 10/1996 |
| WO | WO 97/03609 | 2/1997 |
| WO | WO 97/29682 | 8/1997 |
| WO | WO 99/07284 | 2/1999 |
| WO | WO 99/27837 | 6/1999 |

OTHER PUBLICATIONS

Detmer et al., "3D Ultrasonic Image Feature Localization Based on Magnetic Scanhead Tracking: In Vivo Calibration and Validation", 1994.

\* cited by examiner

*Primary Examiner*—Robert Raevis
(74) *Attorney, Agent, or Firm*—Eitan, Pearl, Latzer & Cohen Zedek, LLP.

(57) ABSTRACT

There are disclosed systems for calibrating a first position measuring component on an imaging or scanning transducer with respect to the scanning plane. Calibrations are performed by using a calibrating device including an additional or second position measuring component, such that during the calibration process, the relative position of between these position measuring components can be calculated. Calibrations are also performed by viewing targets on the scanning plane that are at a known position with respect to the second position measuring component. Calibrations are also performed based on the to scanning plane and position measuring component on a guided device, such as a needle, that typically is used in conjunction with the imaging or scanning transducer. Methods for these calibrations are also disclosed.

11 Claims, 20 Drawing Sheets z=2cm z=3cm z=4cm z=6cm z=8cm

CALIBRATION METHOD AND APPARATUS FOR CALIBRATING POSITION SENSORS ON SCANNING TRANSDUCERS

CROSS REFERENCE TO RELATED APPLICATION

This application is a divisional of U.S. Ser. No. 09/566,948 filed May 8, 2000, now U.S. Pat. No. 6,311,540, which is a divisional of U.S. Ser. No. 09/220,950 filed Dec. 30, 1998, now U.S. Pat. No. 6,138,495, which is hereby incorporated by reference.

FIELD OF THE INVENTION

The present invention relates to a calibration method and apparatus for calibrating the location and orientation of sensors with respect to the beam plane (scanning plane) of ultrasound scanning transducers. The invention is particularly useful for calibrating position sensors on ultrasound scanning transducers used in medical applications, e.g., for the purpose of guiding insertion devices, such as aspiration and biopsy needles, endoscopes, etc., through body tissue, and is therefore described below with respect to such applications. The invention also relates to calibration of any other component of a position measuring system being attached to an ultrasound transducer or other imaging device, in position measuring systems, that are for example, acoustic, magnetic or optic.

BACKGROUND OF THE INVENTION

In the foregoing medical systems for guiding, e.g., a biopsy needle to a target in body tissue, the part of the body in which the tissue is located is usually imaged by an ultrasound transducer which scans the body along scan planes. The location and orientation of a rigid straight needle, or other insertion device, is determined by a position sensor secured at a predetermined location on the needle. The absolute location and orientation of the plane displayed by the imaging system must also be determined, this being done by a position sensor secured at a given convenient location on the ultrasound scanning transducer. The system enables the measurement of the relative location and orientation of the needle with respect to the target tissue also to be calculated. Once these values are determined, it is possible to compute the expected path of the needle towards the target and to display it on the image in order to enable the physician to navigate the needle precisely towards the target An example of such an imaging system is described in our Patent Application No. PCT/IL96/00050 published Feb. 6, 1997, which is hereby incorporated by reference.

In such a system, the position sensor, secured to a predetermined point on the needle, measures the precise location and orientation of the needle upper tip but the position sensor, being attached to the ultrasound transducer at a convenient, arbitrary location thereon, does not have a well determined spatial position and orientation to the scan plane of the transducer so as to precisely relate the transducer position sensor to the transducer scan plane. Yet, since the navigation of the needle to the target uses the ultrasound image as a background for the display of the future path of the needle, it is imperative to calculate the precise location and orientation of the scan plane with respect to the position sensor on the ultrasound transducer.

A method described in relation to calibrating a magnetic position sensor being affixed to an ultrasound transducer is described in, Detmer et al., in "3D Ultrasonic Image Feature Localization Based on Magnetic Scanhead Tracking. In Vitro Calibration and Validation. This method has the drawback that the ultrasound transducer must be maneuvered at a relatively large number of positions, and complicated mathematical algorithms are employed in order to resolve ultrasound beam plane orientation with respect to the target. The methods presented herein alleviate these aforementioned drawbacks, by utilizing ultrasound target(s) that are known and fixed spatially with respect to a position measuring component.

OBJECTS AND SUMMARY OF THE INVENTION

An object of the present invention is to provide a method and apparatus for calibrating a scanning transducer, particularly an ultrasound scanning transducer (ultrasound transducer), in order to calculate the precise location and orientation of its scan plane with respect to the position sensor on the ultrasound transducer.

According to one aspect of the present invention, there is provided a method of calibrating a transducer, outputting a scanning beam for scanning a body along a scanning plane through the body, which transducer has a first position sensor attached to it at a fixed location thereon for measuring the location and orientation of the transducer position sensor with respect to the scanning plane, comprising the operations:

(a) actuating the transducer to scan a body or body volume along a scanning plane or volume while measuring the location and/or the orientation of the position sensor with respect to a fixed reference point in space, (b) utilizing a second position sensor to measure the location and orientation of the scanning plane with respect to the reference point in space while the transducer scans the body along the scanning plane, (c) and computing, from the measurements produced in operations (a) and (b), a value representing the location and orientation of the transducer scanning plane with respect to the first position sensor for use in calibrating the first position sensor according to the position at which it is fixed on the transducer.

According to additional aspects of the present invention, the second position sensor can be replaced by a transmitter and the position of the first position sensor, being attached to the ultrasound transducer, is calculated with respect to this transmitter According to additional aspects of the present invention, the position sensor affixed onto the ultrasound transducer is some other component of a position measuring system (transmitter/reflector) and the second position sensor is some other component of the position measuring system; such that the relative position between the above two position system measuring components can be measured directly or through measurement relative to a reference location in space, in accordance with the systems detailed in PCT/IL96/00050 and PCT/IL98/00578, PCT/IL98/000578 also incorporated by reference in its entirety herein.

Examples of the invention are now described below.

In one described embodiment, operations (a) and (b) are performed by using a calibration device defining a reference plane, which calibration device includes the second position sensor (or other suitable position measuring component, for example transmitters, receivers, reflectors, transceivers, etc), and by aligning the scanning plane of the transducer with the reference plane in the calibration device.

In the second described embodiment, the second position sensor (or other suitable position measuring component) is located, when operation (b) is performed, on a device which is manipulated to sense at least three non-collinear points defining the transducer scanning plane, and to measure the location and orientation of the three points with respect to the fixed reference point in space. For example, where the device is a medical device such as a biopsy needle, the second position sensor would be at known location on the biopsy needle with respect to its tip.

According to a further aspect of the present invention, there is provided apparatus for calibrating a transducer in accordance with foregoing methods.

According to a still aspect of the present invention particularly useful in the first embodiment, there is provided a calibration device for calibrating a position sensor on and with respect to an ultrasound transducer used for scanning a body along scanning planes through the body, comprising:

a charmer filled with a liquid having ultrasonic propagation properties similar to those of the body to be scanned;

a wall of the chamber being formed with an opening covered by an acoustical matched membrane adapted to receive the ultrasonic transducer having the position sensor to be calibrated;

and a plurality of at least three non-collinear echogenic elements located within the chamber at predetermined locations therein so as to define a reference plane within the chamber such as to enable the location and orientation of the position sensor to be calculated with respect to the scan plane of the ultrasound transducer.

According to further features in the latter described embodiment, the chamber is in the configuration of a right rectangular prism, including first and second lateral walls, first and second end walls, a top wall, and a bottom wall. The plurality of echogenic elements include first and second groups of small cross-section rods of echogenic material secured to said first and second lateral walls, respectively, and extending perpendicularly thereto inwardly of the chamber, the rods of each group being non-aligned with respect to the rods of the other group and having free tips located at said reference plane within the chamber.

According to other aspects of the present invention, particularly useful in the first embodiment, the chamber can have any form that does not introduce image distortion to the ultrasound image, and/or the echogenic targets are lines or polygons or other shapes, that can be arranged in a manner that defines a reference plane.

As will be described more particularly below, the calibration method and apparatus of the present invention enable transducers to be calibrated so as to precisely determine the location and orientation of the scan plane with respect to the position sensor (or other position measuring component) on the transducer. Once this has been determined with respect to a position sensor secured on the transducer, this calibration data remains the same for the respective transducer until the location of the position sensor on the transducer is changed, whereupon the transducer must be recalibrated.

The present invention can be used for calibrating any component of a position measuring component being attached to an ultrasound transducer. In particular, the present invention can be used for calibrating any component of a position measuring component being attached to an ultrasound transducer, in conjunction with the guiding systems disclosed in PCT/IL96/00050 and PCT/IL98/00578.

Further features and advantages of the invention will be apparent from the description below.

BRIEF DESCRIPTION OF THE DRAWINGS

The invention is herein described, by way in example only, with reference to is the accompanying drawings, wherein like reference numerals indicate corresponding or like components. In the drawings:

FIG. 4 is a transverse view of a vertical section through the calibration device illustrated in FIG. 2a;

FIGS. 5a–5e are views of horizontal sections taken at five different elevations through the calibration device of FIG. 2a;

FIG. 6 is a schematic view illustrating the desired ultrasound image for ultrasound transducers having relatively short penetration depths, e.g. up to 8 cm, using the device of FIG. 2a;

FIG. 7 is a schematic view illustrating the desired ultrasound image for transducers having larger penetration depths e.g. of more than 8 cm, using the device of FIG. 2a;

DESCRIPTION OF THE PREFERRED EMBODIMENTS

Figure 1A:
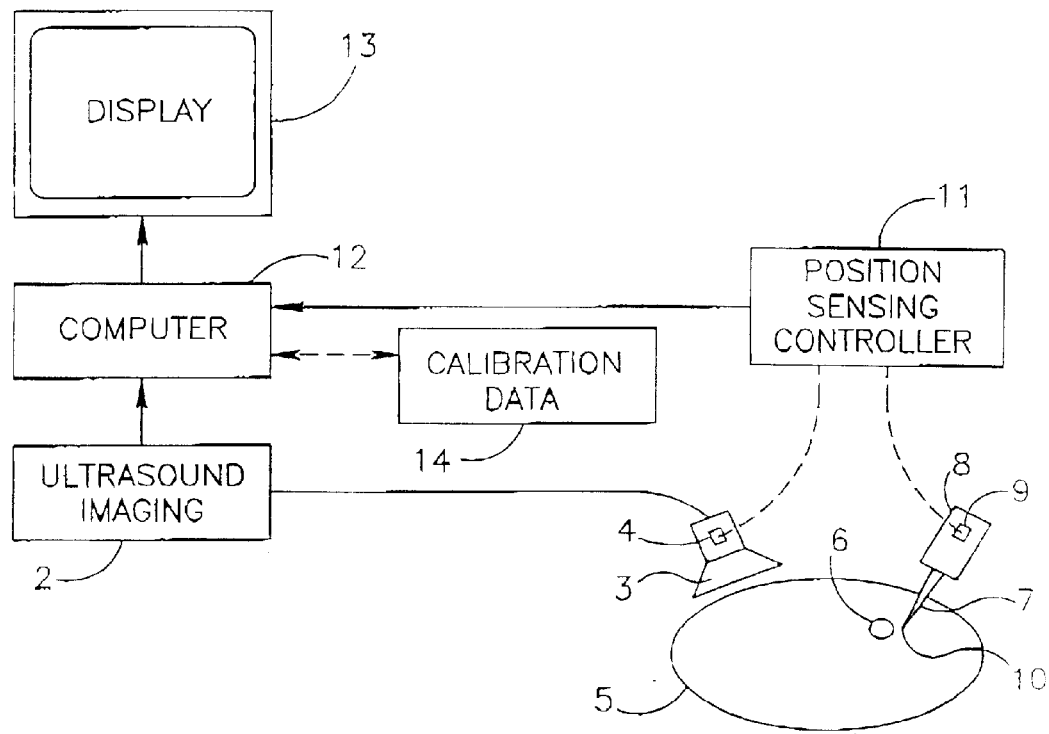
FIG. 1a illustrates one form of guiding imaging system in which the calibration device and method of the present invention are particularly useful.

With reference to FIG. 1a, there is illustrated a guiding system to be employed with an ultrasound imaging system, generally designated 2, including an ultrasound transducer 3, carrying a position measuring component, here a position sensor 4 attached at a convenient, arbitrary location thereon, which ultrasound transducer 3 is used for scanning a body 5 along scan planes through the body. For example, the body 5 (or body volume) may be tissue of a subject having a target 6 to which a needle 7 is to be directed in order to perform a biopsy. The needle 7 is carried by a needle holder 8 also having a position sensor 9 fixed to it. The location and orientation of the tip 10 of the needle 7 is precisely known beforehand with respect to the position sensor 9 carried by the needle holder 8, so that by detecting the location of the position sensor 9, the relative location and orientation of needle 7 with respect to the target tissue 6 can be calculated. The later calculation is executed in a position sensing controller 11.

Position sensing controller 11 also calculates the location and orientation of the ultrasound transducer sensor 4 and feeds the calculations to a computer 12. Computer 12 also receives an input from the ultrasound imaging system 2, and computes the expected path of the needle 7 towards the target 6. This expected path is displayed on a display 13 to enable the physician to navigate the needle to the target 6 when taking a biopsy.

Figure 1B:
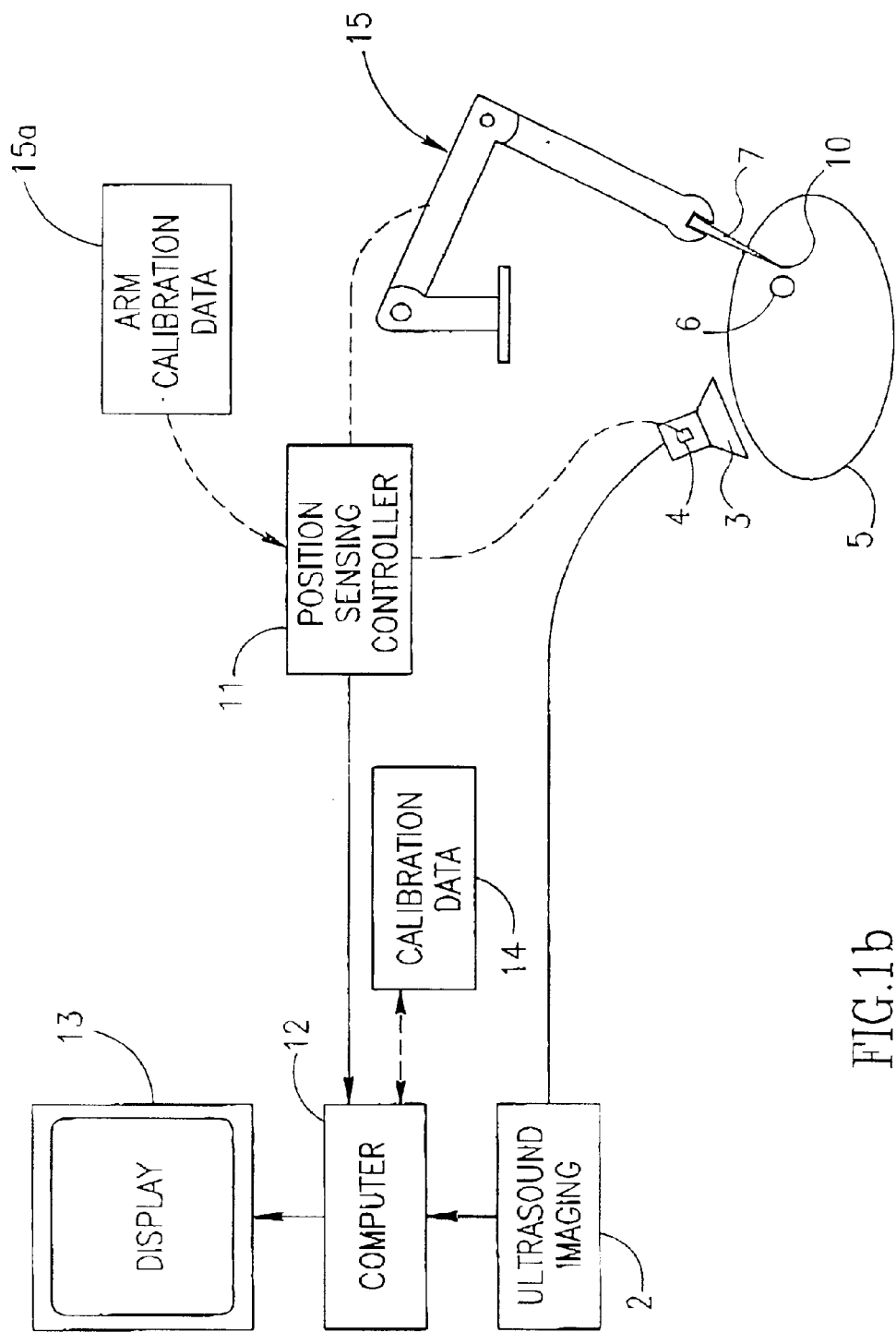
FIG. 1b illustrates another form of guiding imaging system in which the calibration device and method of the present invention are particularly useful.

Further details of the construction and operation of such a system as illustrated in FIGS. 1a and 1b, as well as variations in the systems, are described in the above cited Patent Application PCT/IL96/00050 published Feb. 6, 1997, incorporated by reference in its entirety herein.

According to additional features, the position sensor 4 on the ultrasound transducer 3 could be a transmitter and the position sensor 9 on the guided device, here the needle holder 8, could be a receiver, in accordance with the system detailed in PCT/IL98/00578, incorporated by reference in its entirety herein. Further details of the construction of such a system, as well as variations in the system, are described in this PCT/IL98/00578.

As indicated earlier, while the position sensor 9 secured to the needle holder 8 measures the precise location and orientation of the needle 7 and its tip 10, the, position sensor (position measuring component) 4 secured to the ultrasound transducer 3 does not have a well determined spatial relationship with the plane of the ultrasound scan (the scanning plane). The present invention calibrates the location and orientation of the ultrasound scanning plane with respect to the position sensor 4 (position measuring component) the ultrasound transducer 3. The resultant data is used for calibration and is stored at 14 (preferably a database electronically linked to the computer 12).

In FIG. 1b, there is shown a medical imaging system with the needle 7 positioned on an articulated arm 15, the arm 15 as described in U.S. Pat. No. 5,647,373, incorporated by reference in its entirety herein, and PCT/IL98/00578, such that its position can be measured with respect to the ultrasound transducer 3. The remainder of the system Is in accordance with that detailed in FIG. 1a above, with the arm calibration data stored at 15a. In accordance with the present invention,, the needle 7 on the articulated arm 15, is calibrated with the position measuring system that is tracking the ultrasound. Further details of the construction of such a system as illustrated in FIG. 1b, as well as variations in the system, are described in our PCT/IL98/00578.

The ultrasound transducer 3, in the above detailed systems of FIGS. 1a and 1b, is calibrated, according to one embodiment of the present invention, by performing the following operations:

(a) actuating the ultrasound transducer to scan a body or body volume along a scanning plane or volume while measuring the location and/or the orientation of the position sensor with respect to a fixed reference point in space;

(b) utilizing a second position sensor to measure the location and orientation of the scanning plane with respect to said reference point in space while the transducer scans the body along the scanning plane; and (c) computing, from the measurements produced in operations (a) and (b), a measurement of the location and orientation of the transducer scanning plane with respect to the transducer position sensor for use in calibrating the transducer position sensor according to the location at which it is fixed on the transducer.

This calibration data is stored at 14 and is used during the clinical do examinations as described below. Once the ultrasound transducer 3 has been calibrated, it is not necessary to recalibrate it unless and until the location of its position sensor is changed with respect to the scanning plane of the transducer 3.

Figure 2A:
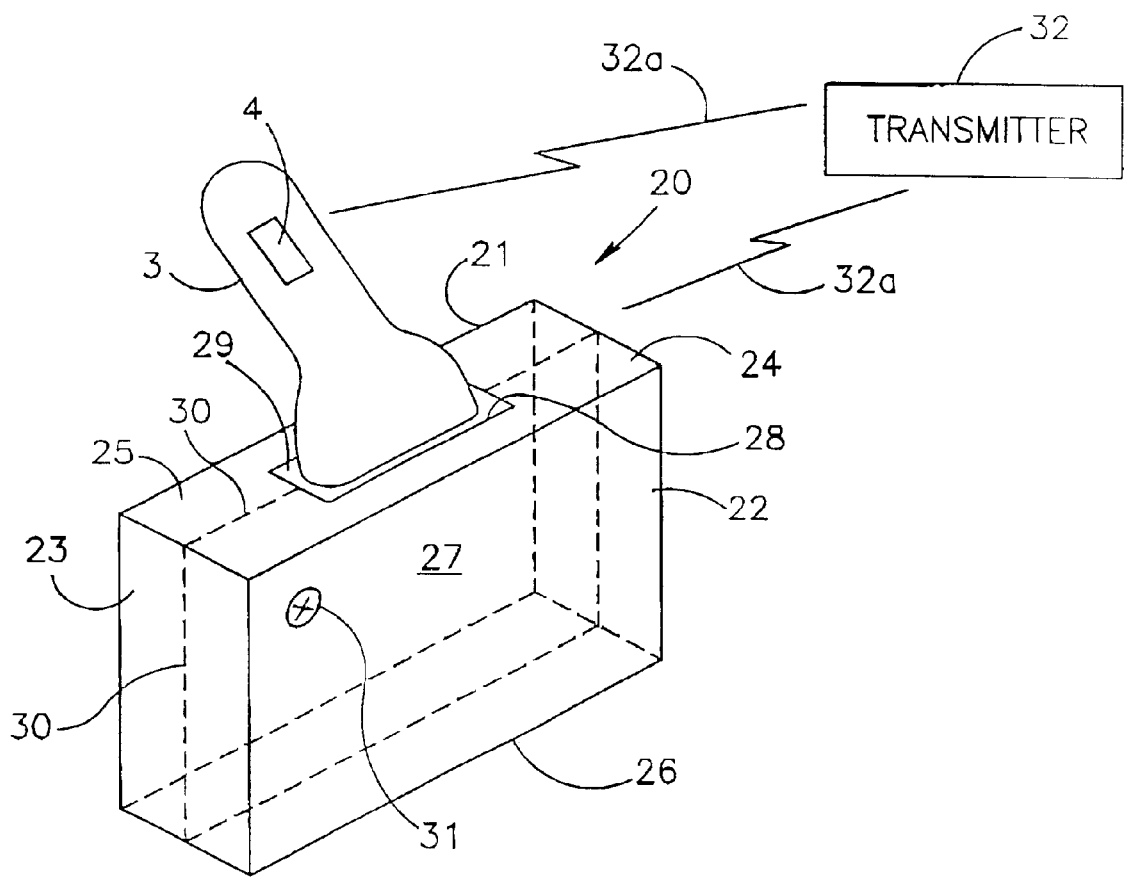
FIG. 2a is a three-dimensional view illustrating one form of a calibration assembly and a calibration device constructed in accordance with the present invention.

FIGS. 2a–2g and 3–7 illustrate methods, and also a device useful in such method, for calibrating the ultrasound transducer in accordance with the present invention. FIG. 2a shows the system of FIG. 1a in a calibration operation, as the scanning plane, emitted as a function of the beam 36 (FIGS. 6, 7, 8a, 9a, 9b, 15b and 16b) of the ultrasound transducer 3 is calibrated with respect to the position measuring component, here a position sensor 4, attached to the ultrasound transducer 3. This method shown in FIG. 2a is exemplary of methods that employ devices for calibrating the ultrasound transducer 3. FIG. 2a as well as FIGS. 2b and 2c detail calibration operations performed by "indirect" measurements (detailed below), while FIGS. 2d–2g detail calibration operations performed with "direct" measurements (detailed below).

With specific reference to FIGS. 2a, 3, 4, 5a–5e, 6 and 7, there is detailed a first calibration method, that utilizes a calibration device. This calibration device includes a chamber, generally designated 20, in the configuration of a right rectangular prism having a first lateral wall 21, a second lateral wall 22, a first end wall 23, a second end wall 24, a top wall 25, and a bottom wall 26, all of rectangular configuration. The interior 27 of chamber 20 is filled with a liquid having ultrasound propagation properties similar to those of the target. For example, where the body to be scanned is a biological tissue, the liquid filling its interior 27 is preferably glycol, but could be any other liquid whose properties of ultrasound propagation are similar to those of biological tissue Should the liquid have properties different than those of biological tissue, this difference in properties must be accounted for when calibrations are performed. The walls 21–26 of the chamber 20 may be made, for example, of Plexiglas, or any other material that ensures against distortion from the ultrasound beam.

The top wall 25 of chamber 20 is formed centrally with a rectangular opening 28 covered by an acoustical matched membrane 29 over which the ultrasound transducer 3 (hardwired connections from the ultrasound transducer 3 to other components are not shown in FIG. 2*a*) is to be placed in order to scan the interior of the chamber. Alternately, acoustic top walls can be used on the chamber 20, such to prevent against distortion from the ultrasound beam.

Each of the two lateral walls 21–22 includes a group of echogenic elements, namely elements which reflect the ultrasound waves from the ultrasound transducer 3. These elements are in the form of small cross-section rods of echogenic material. They are secured to the respective lateral wall and extend perpendicularly thereto inwardly of the chamber 20 to a plane, schematically indicated at 30 in FIGS. 2*a* and 4, which is exactly midway between and parallel to the two lateral walls. This plane 30 defines the reference plane of the calibration device. The chamber 20 further includes a position measuring component 31, such as a transmitter, receiver, reflector, transceiver, etc. that is at a known position (and thus, a known distance) from the reference plane 30.

The location and orientation of a position measuring component 31, here a position sensor, preferably a receiver, is measured during the calibration process with respect to the transmitter, shown at 32 (communicating along path 32*a*), which is fixed in space and therefore serves also as the reference point for position sensor 4 on the transducer 3 (also communicating along path 32*a*). Thus, since the position and orientation of sensor 31 are known with respect to the reference plane 30, when the position and orientation of sensor 31 are determined with respect to the reference point in space (transmitter 32), the position and orientation of the reference plane 30 can be determined with respect to the reference point in space (transmitter 32). If the transducer scanning plane can be aligned with reference plane 30, and since the position and orientation of transducer sensor 4, preferably also a receiver, are also known with respect to the reference in space (transmitter 32) the position and orientation of sensor 4 can be determined with respect to the ultrasound scanning plane (detailed below).

FIGS. 3, 4, 5*a*–5*e*, 6 and 7 more particularly illustrate possible locations and orientations of echogenic targets used to define the reference plane 30, that can be used to define the position of the scanning plane for the for the calibrations detailed in FIGS. 2*a*–2*g*. In the embodiments disclosed in these figures, the lateral walls 21, 22 include echogenic elements secured to the lateral walls 21 and 22, respectively. Thus, lateral wall 21 includes six echogenic rods 21*a*–21*f*, and lateral wall 22 includes four echogenic rods 22*a*–22*d*, respectively. All the echogenic rods 21*a*–21*f* and 22*a*–22*d* are of the same cylindrical configuration and have an outer diameter of less than the resolution of the ultrasonic imaging system; preferably, they are of 2 mm in outer diameter with a linear manufacturing tolerance of 0.1 mm and an angular manufacturing tolerance of 0.1°.

Figure 3:
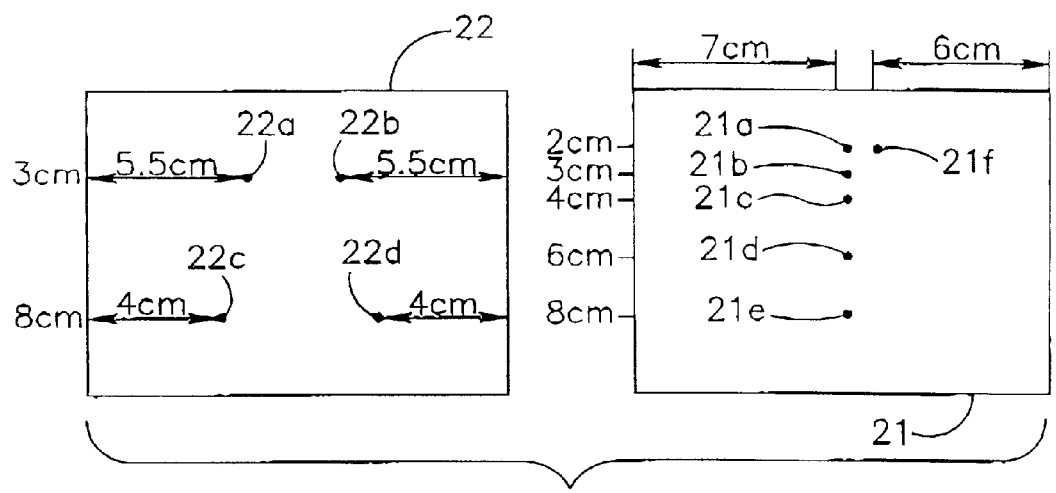
FIG. 3 illustrates the two lateral walls in the calibration device of FIG. 2a, and the locations of the echogenic elements mounted on those walls.
Figure 4:
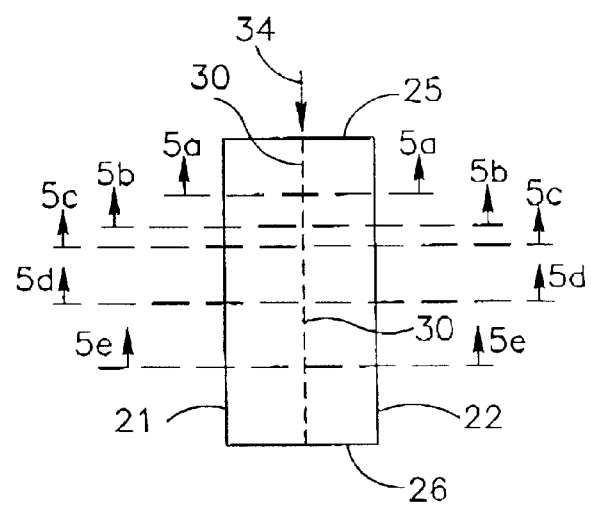
Figure 5A:
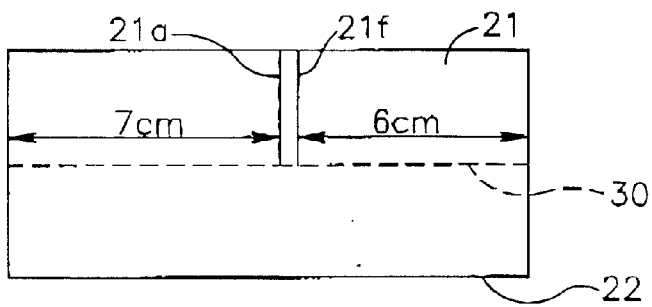
Figure 5B:
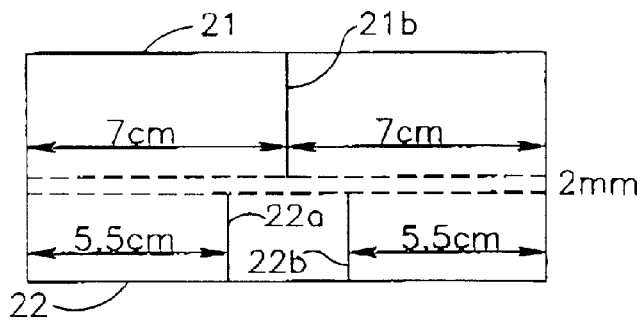
Figure 5C:
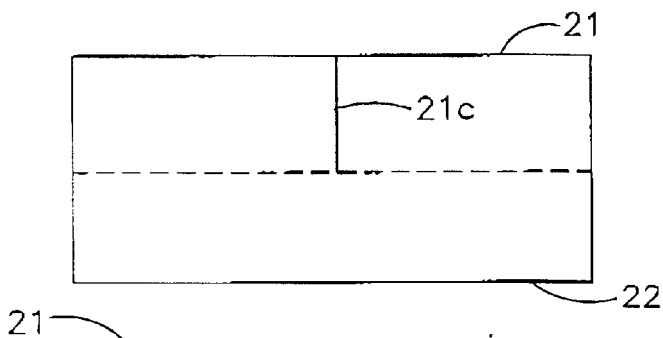
Figure 5D:
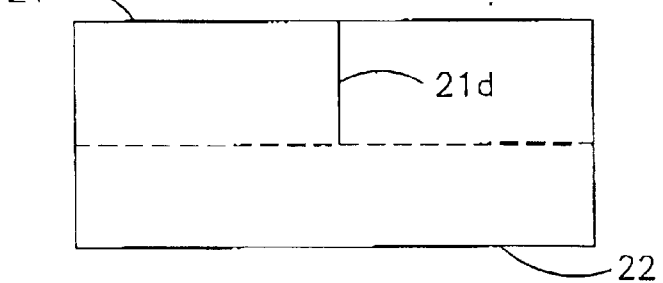
Figure 5E:
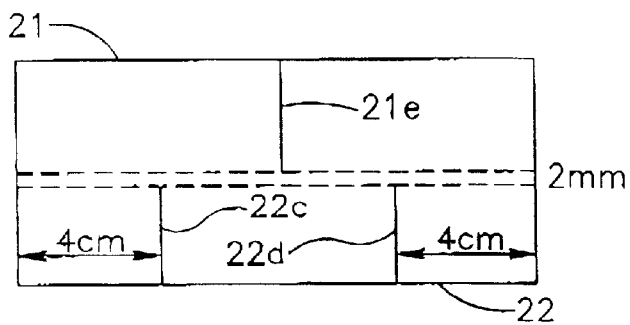

As shown particularly in FIGS. 3 and 4, the six echogenic rods 21*a*–21*f* secured to lateral wall 21 consist of five rods 21*a*–21*e* in vertical alignment with each other, and a sixth rod 21*f* in horizontal alignment with the uppermost rod 21*a*. The four echogenic rods 22*a*–22*d* secured to lateral wall 22 consist of an upper pair of horizontally-aligned rods 22*a*–22*b*, and a lower pair of horizontally aligned rods 22*c*–22*d* spaced closer to the end walls 23, 24 than the upper pair of rods 22*a*, 22*d*. None of the rods 22*a*–22*d* secured to lateral wall 22 is in alignment with any of the rods 21*a*–21*f* secured to lateral wall 21. The free tips of all the rods are located in the reference plane 30.

In the example illustrated in FIGS. 2*a* and 3–7, one chamber 20 that may be used for the calibration process is 14 cm in length, 11 cm in height, and 7 cm in width, the five echogenic rods 21*a*–21*e* are secured to the lateral wall 21 at spacings of 2 cm 3 cm, 4 cm, 6 cm and 8 cm, respectively, from the top wall 25 and 7 cm from the end wall 23; the sixth echogenic rod 21*f* secured to lateral 21 is located in horizontal alignment with rod 21*a* and 6 cm from end wall 23; the upper pair of echogenic rods 22*a*–22*b* are located 3 cm from the top wall 25 and 5.5 cm from the two end walls 22, 23; and the lower pair of echogenic rods 22*c*, 22*d* are secured to lateral wall 22, 8 cm from the top wall 25, and 4 cm from the respective end walls 22, 23. This chamber 20 can also be used in the calibration operations detailed in FIGS. 2*b*–2*g* below.

FIGS. 5*a*–5*e*, which are horizontal sections at distances of 2 cm (FIG. 5*a*), 3 cm (FIG. 5*b*), 4 cm (FIG. 5*c*), 6 cm (FIG. 5*d*) and 8 cm (FIG. 5*e*), respectively, more particularly illustrate the locations and orientations of the six echogenic rods 21*a*–21*f* secured to lateral wall 21, and the four echogenic rod 22*a*–22*d* secured to lateral wall 22.

The manner of using the calibration device illustrated in the drawings for calibrating the ultrasound transducer 3, particularly the location and orientation of its scan plane (the scanning plane) with respect to its position sensor 4, will now be described with reference to the schematic diagrams of FIGS. 6 and 7.

Figure 6:
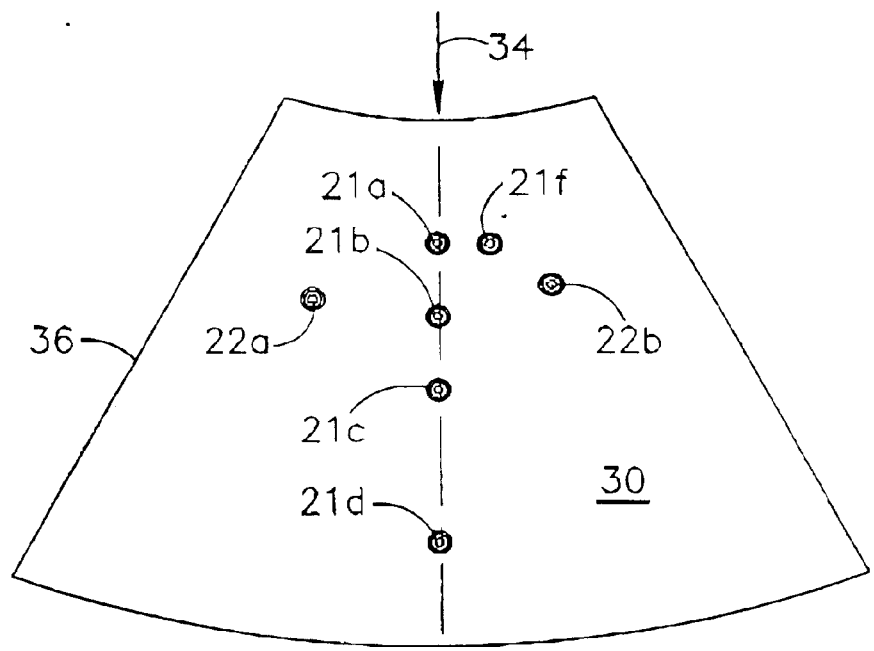
Figure 7:
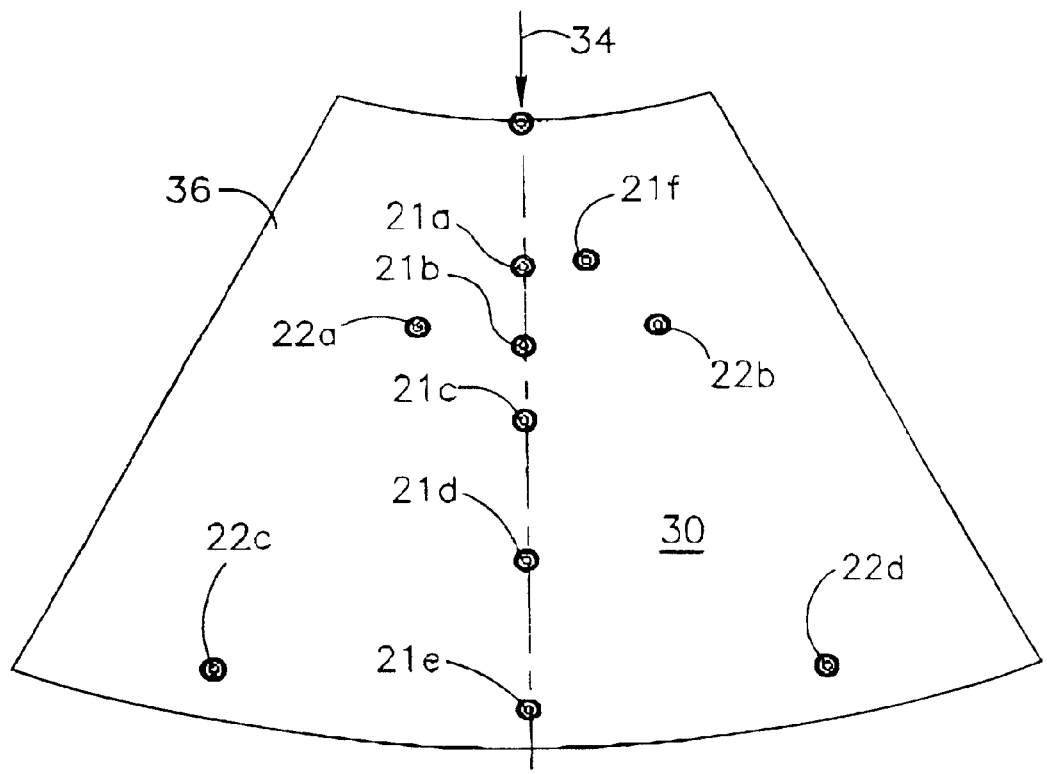

When using the calibrating device illustrated in FIGS. 2*a* and 3–5, the ultrasound transducer 3 is placed on top of membrane 29 and is manipulated until the pattern shown in FIG. 6 for short penetrating ultrasound transducers, or in FIG. 7 for deep penetrating ultrasound transducers, is obtained. For this purpose, the ultrasound transducer is moved both in azimuth, i.e. to different angular positions in the horizontal plane of membrane 29, and also in a roll, i.e. rotated about its longitudinal axis, until the pattern of FIG. 6 or that of FIG. 7 is obtained. This information is fed via controller 11 to the computer 12, which determines the location of the center of the fan-shape scan beam and displays same in display 13.

The transducer is further translated until the center of its beam lies on the line connecting the tips of the rods 21*a*–21*e*. The upper pair of rods 22*a*, 22*b* secured to lateral wall 22 aid to orient the transducer in a plane determined by a line connecting them and center line 34 on which the tips of the rods 21*a*–21*e* lie.

Thus, the five vertically-aligned echogenic rods 21*a*–21*e* secured to lateral 21 will define, at their tips, the reference plane 30 of the calibration device, so that when the center line 34 of the scan beam viewing plane (the scanning plane) becomes aligned with the center line of the reference plane 30 defined by the echogenic rods 21*a*–21*e*, the operator signals the computer 12 to record the reading of the transducer center line position 34. This information is recorded in memory unit 14 illustrated in FIGS. 1*a* and 1*b*, Since-all the displayed echoes represent points lying in the same plane, the computer can calculate the relative position and orientation of the set of Cartesian coordinates linked to the position sensor 4 of the transducer with respect to this plane.

Once the scanning plane and the reference plane 30 are coincident, coplanar or the like, their relative position can be determined by the operator from the display 13 or by the computer 12, by image processing algorithms (detailed below). At the same time, when the position of the image or scanning plane is calculated with respect to the reference plane, the relative position between the position measuring components 4, 31 is calculated. The calculation can be performed since the location and orientation of each of the position measuring components 4, 31 is measured with respect to position measuring component 32 being placed at a reference location. In addition, the position of the reference plane is known with respect to the position measuring component 31 (appriori measurement and design of the calibration apparatus.

This relationship allows for the calculation of the position of the beam (scanning plane) with respect to the position measuring component 4 on the ultrasound transducer 3, and hence, the calibration in accordance with the present invention. The calculated positions are then stored as data, that is employed to overcompose an image, typically illustrating the position of a guided device, such as a needle, with respect to the transducer 3 over the image resulting from the beam.

In performing calibrations using the first chamber 20, the upper pair of echogenic rods 22a, 22b, secured to lateral wall 22 aid in orienting the transducer with the reference plane for short penetrating ultrasound transducers, whereas the lower pair of rods aid in orienting the transducer with the reference plane for the deep penetrating ultrasound transducers. The sixth rod 21f secured to lateral wall 21 aids in identifying the left side or right side of the screen.

When employing the calibrating device 20 illustrated in FIG. 2a, first, the position and orientation of the position measuring component (sensor) 31 on chamber 20 is determined with respect to a position measuring component, here a transmitter 32 placed at a reference point; since transmitter 32 is fixed in space, this reference point serves as the reference point in space with respect to the position and orientation measurements of sensor 4 on transducer 3. The calibrating systems illustrated in FIGS. 2b and 2c are based on a similar concept employing the above detailed "indirect" measurements.

For purposes of examples, FIG. 2a illustrates the position measuring component 31, located in the upper left corner of the chamber 20 while in FIGS. 2b–2g, the position measuring component 31 is on a member 31a at a fixed position (known length and orientation) with respect to the chamber 20, and ultimately, the reference plane 30. Either arrangement for the position measuring component 31 is permissible in the calibration set-ups of FIGS. 2a–2g, as the position of this position measuring component 31 remains known with respect to the reference plane 30 of the chamber 20.

Figure 2B:
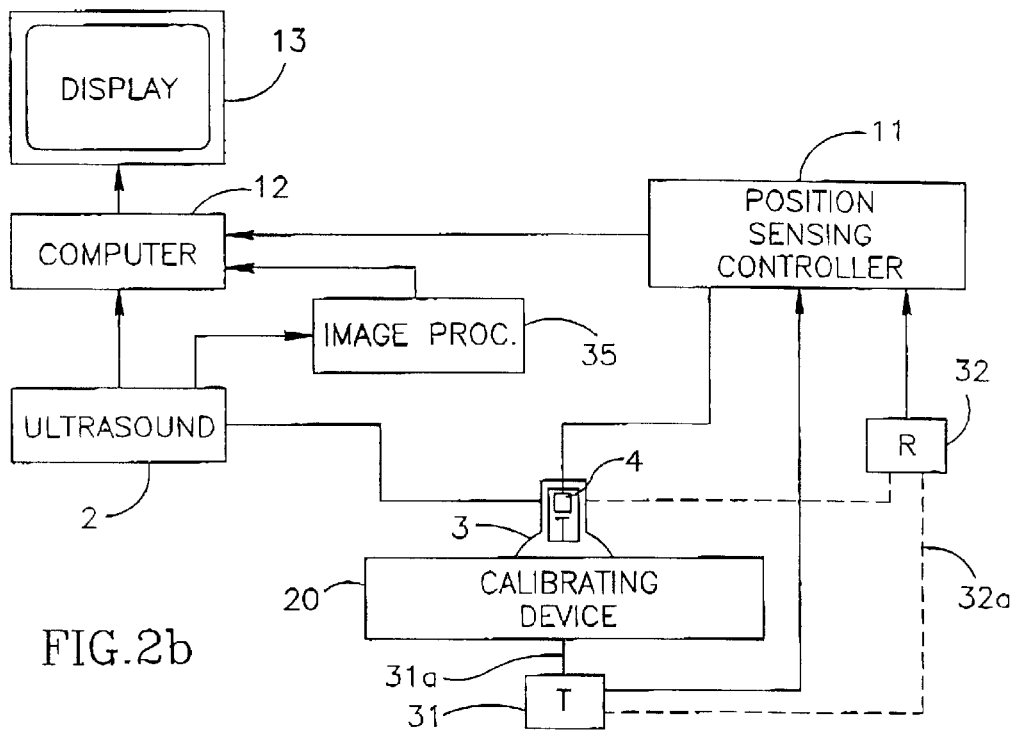
FIGS. 2b–2g illustrate additional calibration assemblies in accordance with the present invention.
Figure 2C:
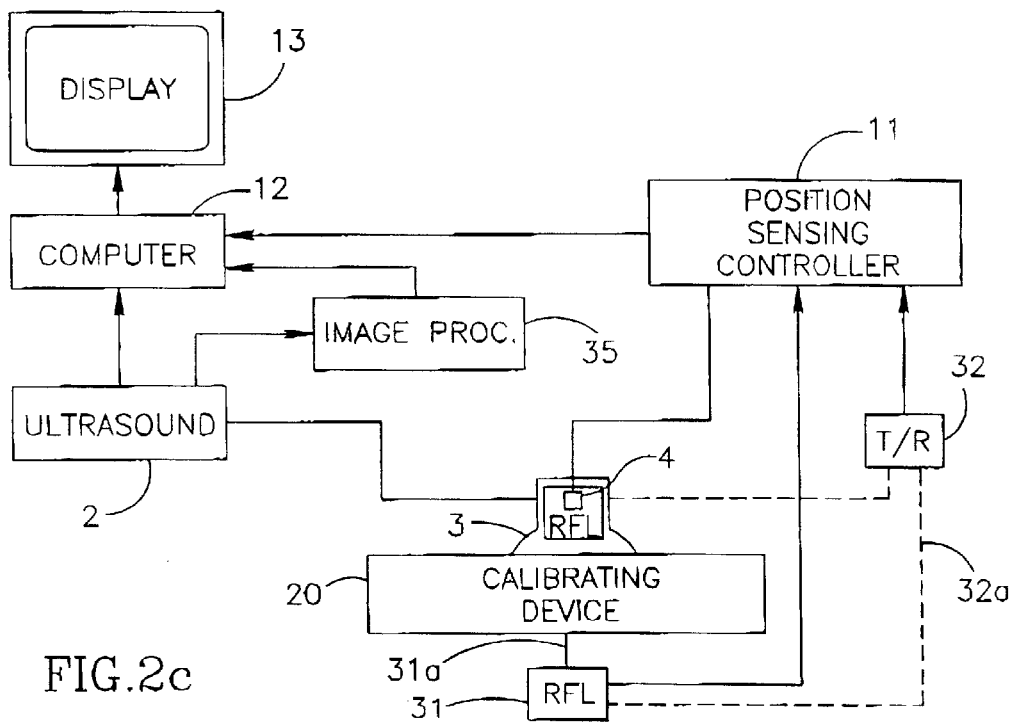

FIGS. 2b and 2c are similar to FIG. 2a, and perform the calibration in a similar manner to that detailed above. Specifically, the relative position between the position measuring components 31, 4 of the chamber 20 and ultrasound transducer 3 (the device to be calibrated), respectively, are measured indirectly, with respect to a position measuring component 32 at a reference location, that is fixed in space. From these calculations of the position measuring component 32 with respect to: 1) the position of the position measuring component 31, and 2) the position measuring component 4 attached to the ultrasound transducer 3, the position of the position measuring components 31, 4, with respect to each other, can be calculated. The differences between the systems are noted.

In FIG. 2b, there is disclosed a system where the ultrasound transducer position sensor (position measuring component) 4 and the position measuring component 31 on the member 31a are transmitters whose location and orientation are measured with respect to a position measuring component 32, typically a receiver, a reference location in space. In FIG. 2c, the system disclosed includes an ultrasound transducer position sensor (position measuring component) 4 and a second position sensor (position measuring component) 31, that are reflectors, whose location and orientation are measured with respect to a reference position, typically occupied by a transceiver, the reflectors and transceivers in accordance with those disclosed in PCT/IL98/00578.

FIGS. 2d–2g are calibrated in accordance with the procedure detailed above, except that the position of the position measuring component 4 on the ultrasound transducer 3 is measured directly with respect to the position measuring component 31 associated with the chamber 20 (attached thereto or on a member 31a). The position measuring components 4, 31 involved with direct measurements are typically transmitter and receiver pairs, although other pairings, including those of transceivers and reflectors are also permissible. These pairings are such that a signal, such as a signal of radiant energy, is generated and received so as to provide positional data. Additionally, if the scanning plane from the beam of the ultrasound transducer 3 can be aligned with the reference plane 30, and since the position of the reference plane 30 is known with respect to the position measuring component 31, the position of the reference plane 30 can be ran calculated with respect to the position of the position measuring component 4, of the ultrasound transducer 3.

Figure 2D:
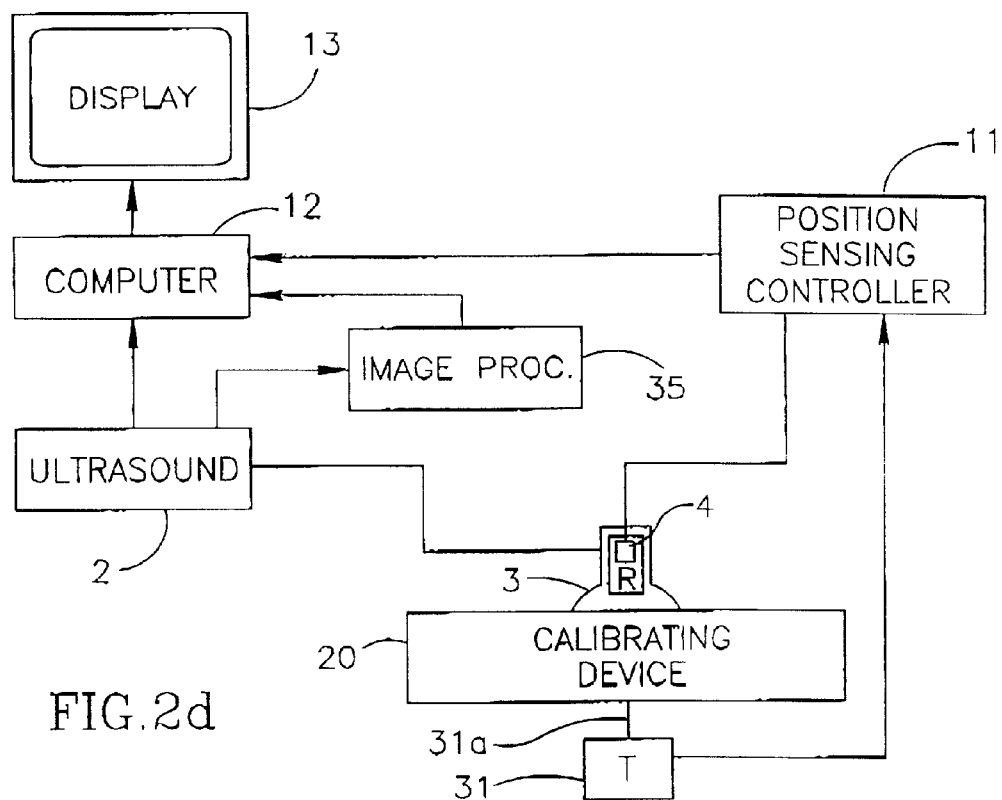

The system detailed in FIG. 2d includes the ultrasound transducer position measuring component 4, as a position sensor, such as a receiver, and the position measuring component 31 on a member 31a is a transmitter. The position of the transducer position sensor 4 is measured directly with respect to the transmitter (position measuring component) 31 associated with the chamber 20.

Figure 2E:
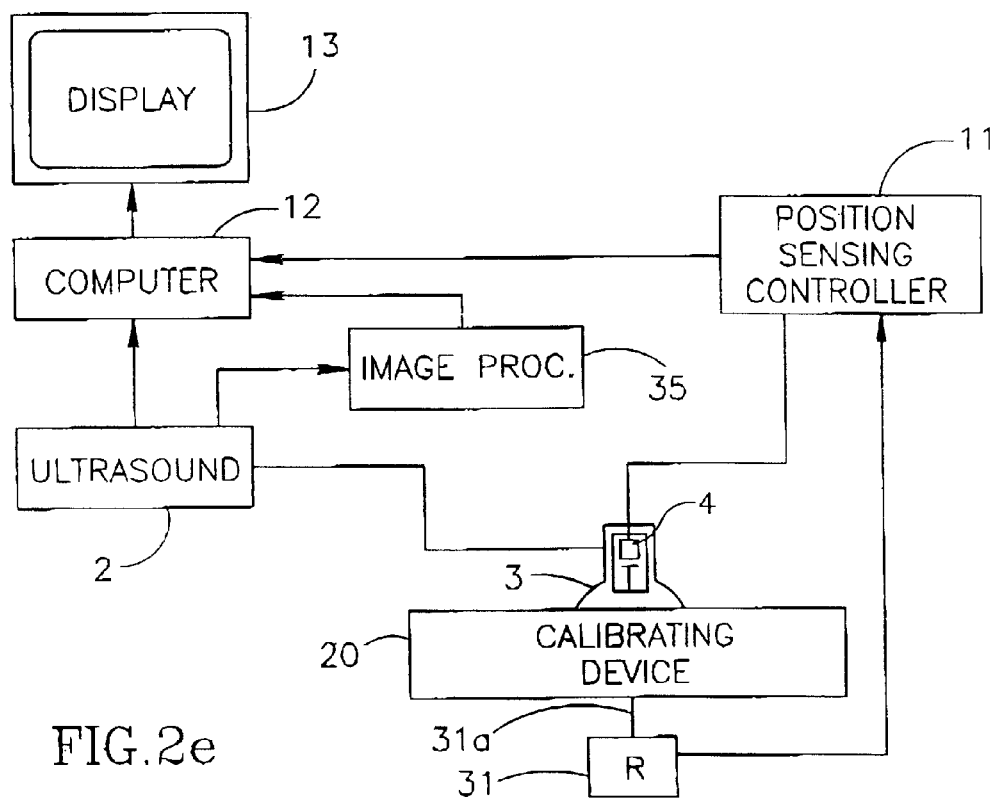
Figure 2F:
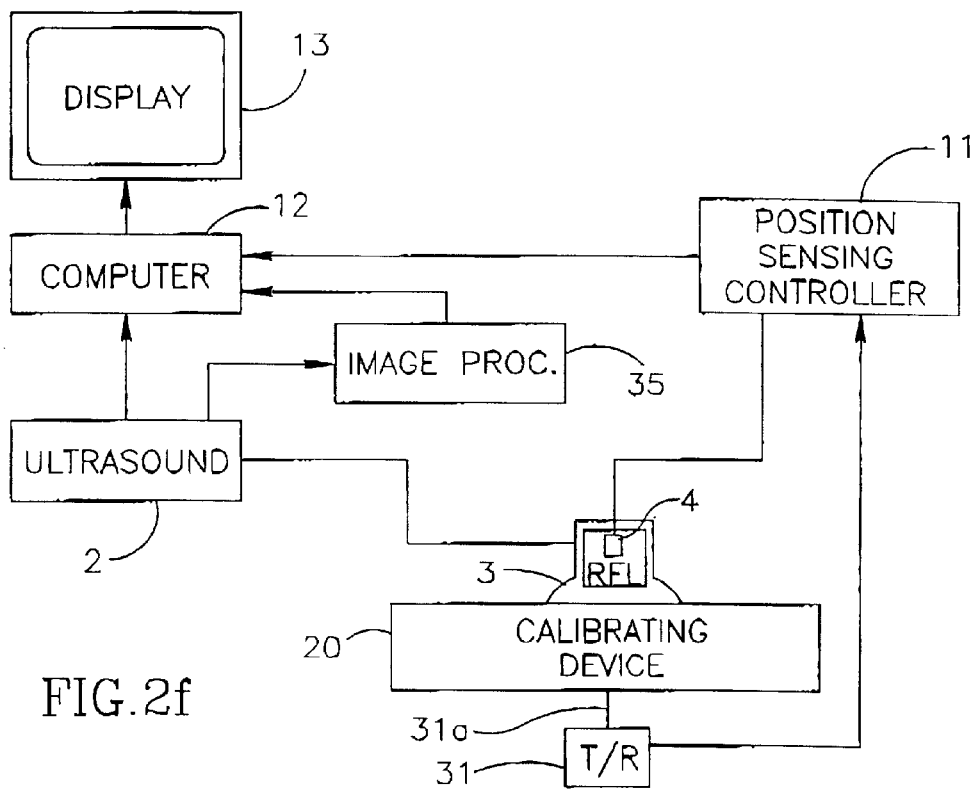
Figure 2G:
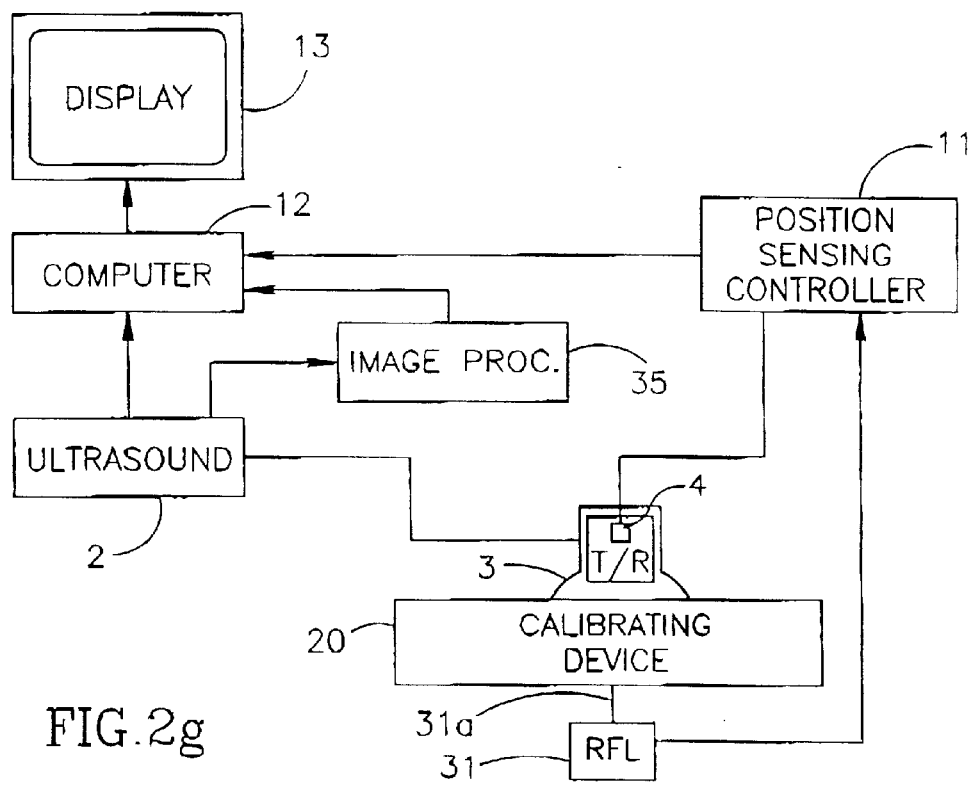

In FIG. 2e, the system is such that the ultrasound transducer position sensor (position measuring component) 4 is a transmitter and the position measuring component 31 on member 31a is a position sensor, such as a receiver. The position of the transducer position measuring component 4 is measured directly with respect to the receiver (position measuring component) 31 on the member 31a. FIG. 2f details a system where the ultrasound transducer position sensor (position measuring component) 4 is a reflector, and the position measuring component 31 on the member 31a is a transceiver, and the position of the transducer position sensor is measured directly with respect to the transceiver. In FIG. 2g, the system disclosed has an ultrasound transducer position sensor (position measuring component) 4 that is a transceiver and a position measuring component 31 on a member 31a, that is a reflector. The position of the ultrasound transducer position sensor is measured directly with respect to the transceiver.

The determination of whether a system like those of FIGS. 2a–2c, involving making an "indirect" measurement, or one like those disclosed in FIGS. 2d–2g, involving a "direct" measurement, with the necessary positional calculations having to be made, depends on the types of devices (for example, a transmitter, receiver, transducer, reflector or transceiver) that are employed for the position measuring components 4, 31, 32 These position measuring components 4, 31, 32 can be part of magnetic, acoustic, optic, or other position measuring systems.

Ultimately, calculations are made such that the position of the position measuring component 4 on the ultrasound transducer 3 is determined with respect to the position measuring component 31 associated with the chamber 20. When the scanning plane of the beam 36 emitted from the ultrasound transducer 3 is substantially coplanar, and preferably coplanar with respect to the reference plane 30, and therefore, at a known position, the position of the scanning plane can be calculated with respect to the position measuring component 31 associated with the chamber 20 (whose position with respect to the reference plane 30 is known, as detailed above). This relationship allows for the calculation of the position of the scanning plane with respect to the position measuring component 4 on the ultrasound transducer 3. This calculated position is then stored as data, that is employed to overcompose an image, typically illustrating the position of a guided device, such as a needle 7 (FIGS. 1a and 1b), with respect to the ultrasound transducer 3 over the image resulting from the beam emitted from the ultrasound transducer 3.

In all of these systems, the components, along with their construction and operation, alone and with respect to each other, are detailed in PCT/IL96/00050 and PCT/IL98/00578 (both of these PCT applications incorporated by reference in their entirety herein). Moreover, FIGS. 17 and 18 (detailed below) illustrate another method and device for calibrating the ultrasound transducer 3 in accordance with at the present invention.

With continued reference to FIGS. 6 and 7, the ultrasound beam 36, that forms the image or scanning plane, while having a relatively thin transverse thickness, still may not define an ideal zero-thickness plane. For this reason, the above-described calibration process can be repeated after the ultrasound transducer 3 has been turned around 180°, and the average recorded values produced by the two procedures is used in calibrating the ultrasound transducer 3 during actual clinical procedures. Additionally, in order to obtain better performance, the procedure may be repeated any number of times. The average recorded value will be the value used for calibration. Moreover, algorithms as well as additional/alternate target clusters may used be used in order to minimize inaccuracies caused by the thickness of the ultrasound beam.

In particular, image processing algorithms can be employed to compensate for potential inaccuracies caused by the thickness of the ultrasound beam 36. For example, these algorithms can check the intensity levels of the targets and/or symmetry in the intensity level of targets and/or relative distances and positions of the targets, and/or size of clusters and/or width of targets and/or symmetry in the width of targets.

In the calibration process above, the target recognition and the decision whether the image plane (scanning plane from the beam of the ultrasound transducer 3) is "in place" with respect to the reference plane 30 (FIG. 2a) (the plane defined by the cluster of echogenic targets) are performed by the operator. These manual tasks can be made easier by employing additional computer assistance functions, as described below.

For example, turning back to FIGS. 2b–2g, the ultrasound image can be processed by an image processor 35 (in communication with the computer 12), that can perform target recognition functions. The computer aided target recognition can be performed according to pattern recognition, for example, by algorithms, that search a specific cluster or clusters, or portions thereof. These algorithms are detailed below. In the automatic process, the computer, by virtue of the image processing software, that for example, operates by comparing the scanned image with a known or control image, automatically calculates the proper ultrasound transducer 3 position.

Additionally, after the automatic target recognition, the determination as to the proper positioning of the ultrasound transducer 3, can be performed by the computer 12. Typically these systems also include software and hardware allowing for a manual overrride of the ultrasound transducer positioning, should it be desired by the operator, based on a visual check of the scan on the display 13.

Additionally, the recognition of portions of the cluster defining the reference plane 30 (FIG. 2a) can be employed to produce indications on the display 13 and enable the operator to manually find the scanning plane rapidly and with a high degree of accuracy and reliability. Also, by viewing the display 13, the operator can mark the desired targets in the image, in accordance with PCT/IL96/00050, resulting from the echoes of the targets on display, enabling the image processor to check whether the operator has properly positioned the scanning plane with respect to the reference plane. Marking the targets in the image resulting from the echoes of the targets on display, enables the image processor (computer 12) to correct inaccuracies caused by the failure of the operator to precisely position the scanning plane coincidental with the reference plane 30 (FIG. 2a).

FIGS. 8a, 8b, 9a and 9b detail target recognition, here, with clusters 80, that requires maneuvering ultrasound transducer 3, such that the scanning plane, from the beam 36, is coplanar with the reference plane 30. Both the reference plane 30 and the scanning plane (from the beam 36) can be defined by three non-coplanar points. For the sake of simplicity, the description below defines a plane formed of three non-collinear points that are virtual points. Specifically, these three virtual points are the origin (Or), a point on the X axes of the plane at distance one unit from the origin labeled as (Ri), and a point on the Y axes at distance one unit from the origin labeled as (Fw). The related Z axes for a right-handed system of coordinates is now defined.

Figure 8A:
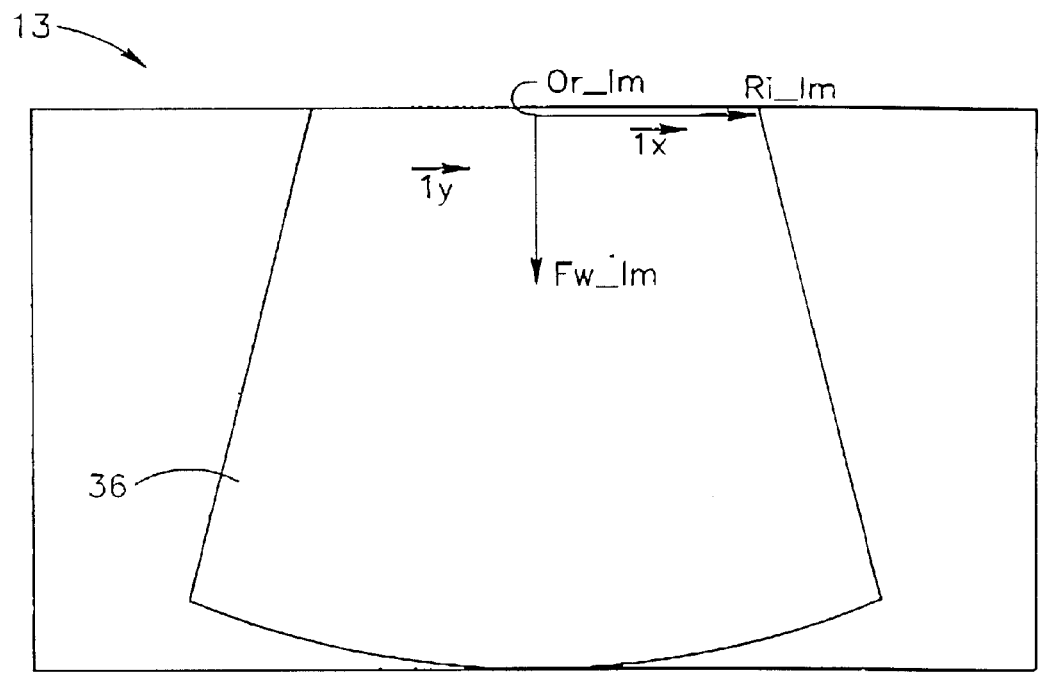
FIG. 8a illustrates three points, defined as an origin, right and forward, in an image (or scanning) plane, mathematically useful in defining the scanning (image) plane.

In FIG. 8a are illustrated the three above defined points determining the image or scanning plane; Or_Im, Ri_Im, Fw_Im. The calibration process finds, or must be enabled, to calculate the position of these three points with respect to the position measuring component 4 attached to the ultrasound transducer 3.

Figure 8B:
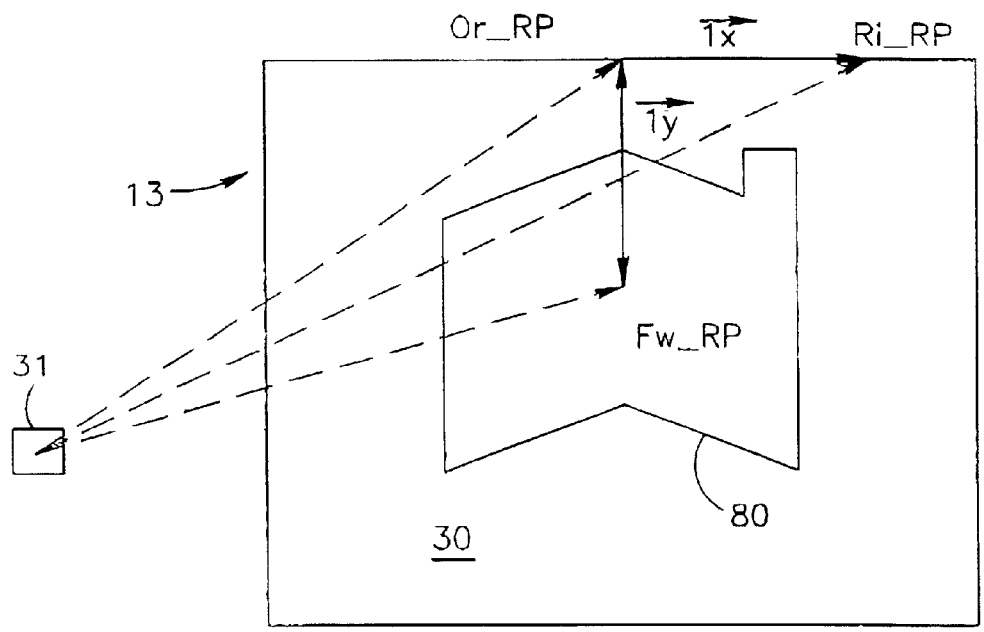
FIG. 8b illustrates three points, defined as an origin, right and forward, in the reference plane for an illustrative target cluster for FIG. 8a mathematically useful in defining the reference plane with respect to the second position measuring component.

In FIG. 8b there are illustrated the three above defined points determining the reference plane: Or_RP, Ri_RF, Fw_RP, with respect to the position measuring component 31 attached to the chamber 20 (or being at known and fixed position from the chamber 20). These three points are at known position with respect to the cluster of targets, or cluster 80. When calibrating the chamber 20 described in FIGS. 3–7, the ultrasound transducer 3 is maneuvered to bring the ultrasound beam 36 and thus, the imaging or scanning plane into a coplanar relationship with the reference plane 30.

The calibration procedures detailed in FIGS. 3–7, may require maneuvering of the ultrasound transducer 3, such that the image or scanning plane is coplanar and coincident with the reference plane 30, whereby their origins are the same as described above. Alternately, these calibration procedures may require maneuvering of the ultrasound transducer 3 such that the image or scanning plane is coplanar with the reference plane 30, whereby their origins do not have to be the same, rather that the clusters 80, or portions thereof, can be imaged by the ultrasound transducer 3.

Figure 10:
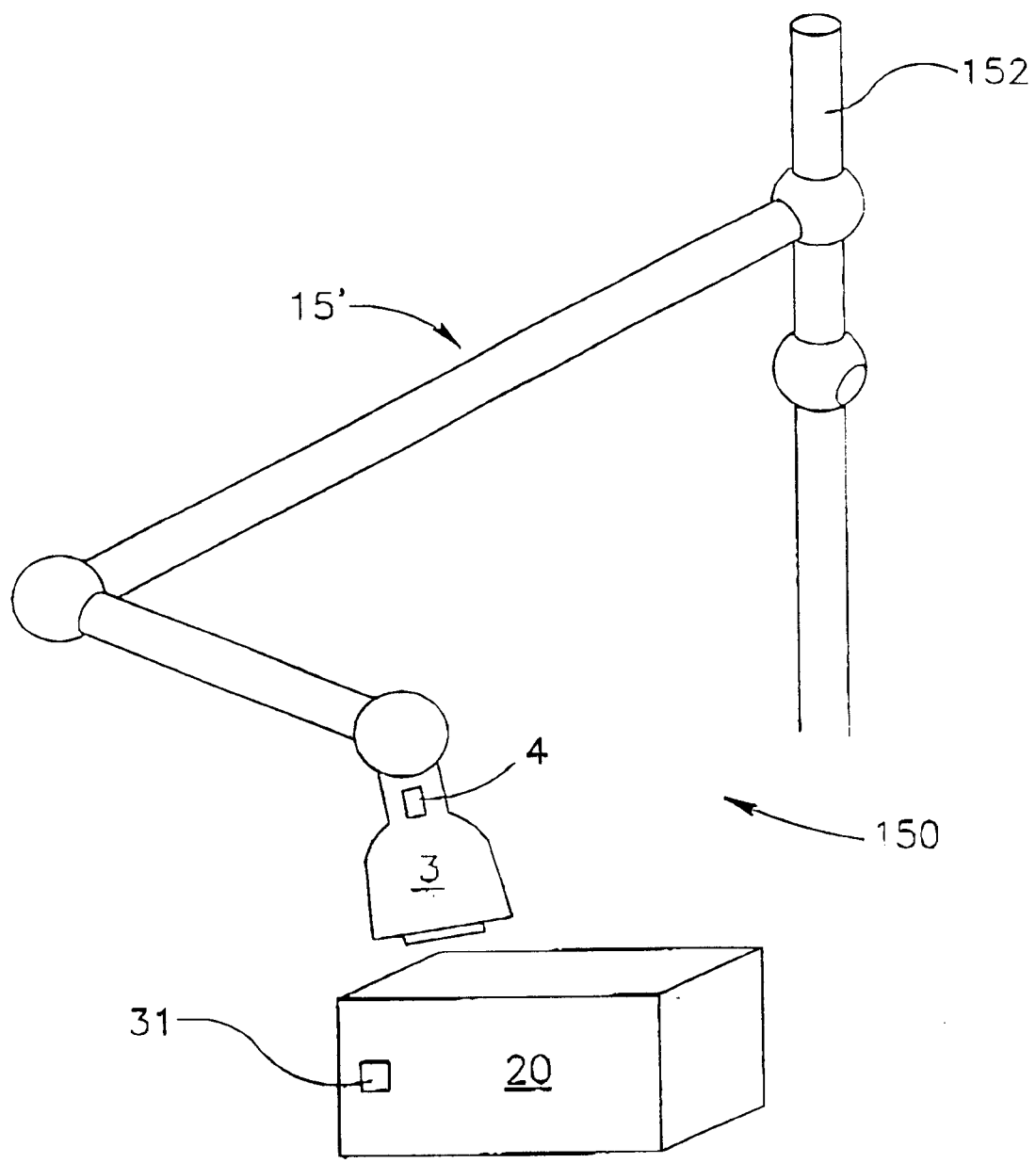
FIG. 10 is a perspective view illustrating the ultrasound transducer on which a calibration operation is performed in accordance with the present invention, as mounted on an arm.

The ultrasound transducer 3 is typically maneuvered manually, for example, as in the calibration operations shown in FIGS. 2a–2g. Alternately, the ultrasound transducer 3 may be moved semi automatically or automatically, for example, as shown by the apparatus 150 of FIG. 10. This apparatus 150 includes an articulated arm 15', similar to arm 15 in FIG. 1b (described above), the arm 15' mounted on a stand 152, in accordance with the stand detailed in U.S. Pat. No. 5,647,373. The arm 15' functions to maneuver the ultrasound traducer 3 with respect to a chamber, such as chamber 20, such that its scanning plane is at the desired location for calibration, in accordance with the calibration procedures detailed herein. The arm 15' is controlled by a computer (not shown), manually, or combinations thereof.

Figure 11A:
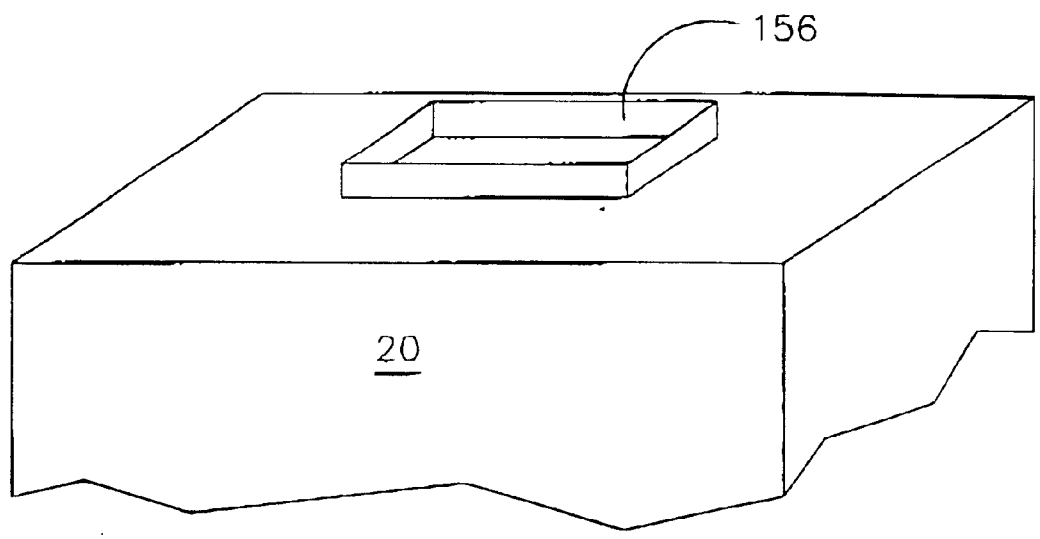
FIGS. 11a and 11b are perspective views of confinements for the ultrasound transducer useful in performing the calibrations in accordance with the present invention.
Figure 11B:
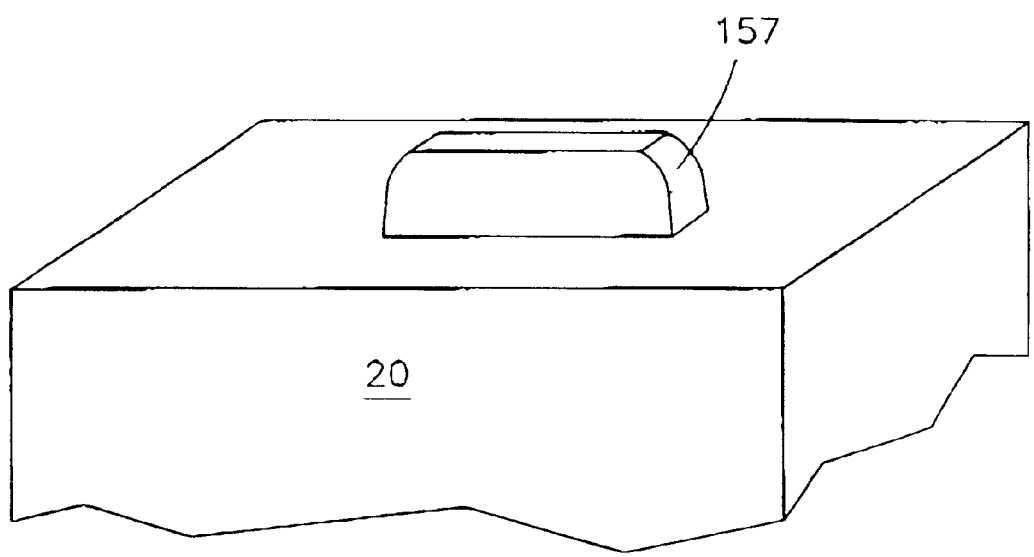

Turning to FIGS. 11a and 11b, the present invention may also include confinements 156, 157 attached to the respective chambers, for example the chamber 20 detailed above. These confinements 156, 157 are shaped to correspond with the shape of the ultrasound transducer 3 (for example in FIG. 2a), to receive and retain the ultrasound transducer, and are positioned on the chamber 20.

In FIG. 11a, the confinement 156 is such that when the ultrasound transducer 3 is placed therein, the ultrasound transducer 3 will be almost "in position" with respect to the reference plane (for example reference plane 30 of the chamber 20 as shown in FIG. 2a) of the chamber 20, therefore necessitating a minimal amount of additional maneuvering. Similarly, in FIG. 11b, the confinement 157 is of an exacting shape and tolerance with respect to the shape of the specific ultrasound transducer 3, such that when the ultrasound transducer 3 is placed therein, the ultrasound transducer 3 will scan the reference plane (for example reference plane 30 of the chamber 20 as shown in FIG. 2a) of the chamber 20, absent additional maneuvering. Moreover, as a result of this confinement 157 the chamber 20 can be modified such that it does not necessitate having echogenic elements 21a–21f, 22a–22d (FIGS. 3, 4, 5a–5e above), since the matching of the scanning plane with respect to the reference plane can be a mechanical match.

Alternately, although not a confinement, the calibration device, such as that shown in FIG. 2a, may have indicia or other markings thereon, corresponding to the position of the reference plane 30 in the chamber 20. In this manner, the ultrasound transducer 3 is placed over the chamber 20, along (in accordance with) the indicia, such that the ultrasound transducer 3 is "in position" or nearly "in position".

Figure 12A:
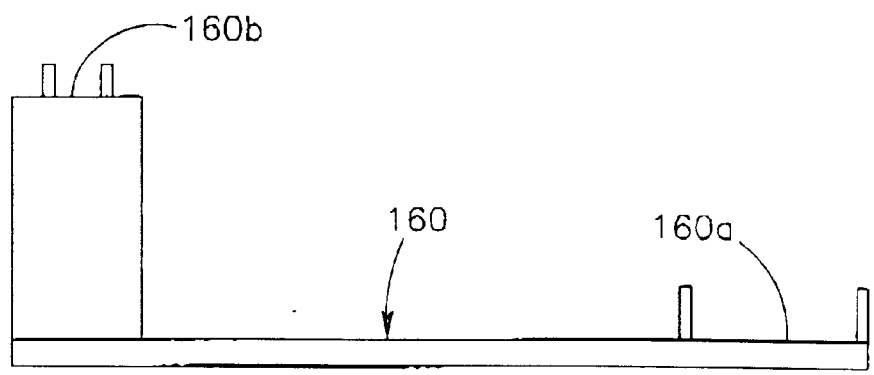
FIGS. 12a and 12b are side views of confinements for the chambers and position measuring components associated therewith useful in performing the calibrations in accordance with the present invention.
Figure 12B:
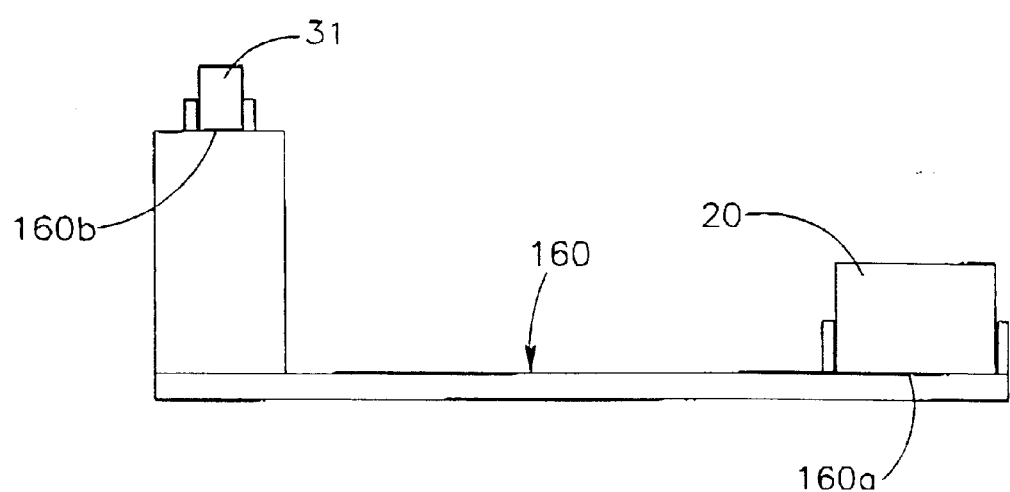

FIG. 12a shows an apparatus 160 having confinements 160a for a chamber, such as chamber 20 and confinements 160b for a position measuring component, such as the position measuring component 31 associated with the chamber 20, as detailed in FIG. 2a. FIG. 12b shows the apparatus 160 with the chamber 20 and position measuring component 31 in their respective confinements 160 a, 160b. This apparatus 160, 161 ensures the exact position of the scanning plane and the reference plane, and the reference plane with respect to the position measuring component 31, since all positions and distances between components and reference planes are known.

Alternately, the target arrangement in the calibrating device 20 can be such that multiple reference planes may be taken therefrom, along which the scanning plane can be aligned. This enables the calibration of the position measuring component 31 on the transducer 3 with respect to the scanning plane by positioning the ultrasound transducer in several positions and then averaging the received values, in accordance with conventional statistical methods.

Turning back to FIGS. 8a, 8b, 9a and 9b, the calibrations involved in the calibration process are described as follows.

Figure 9A:
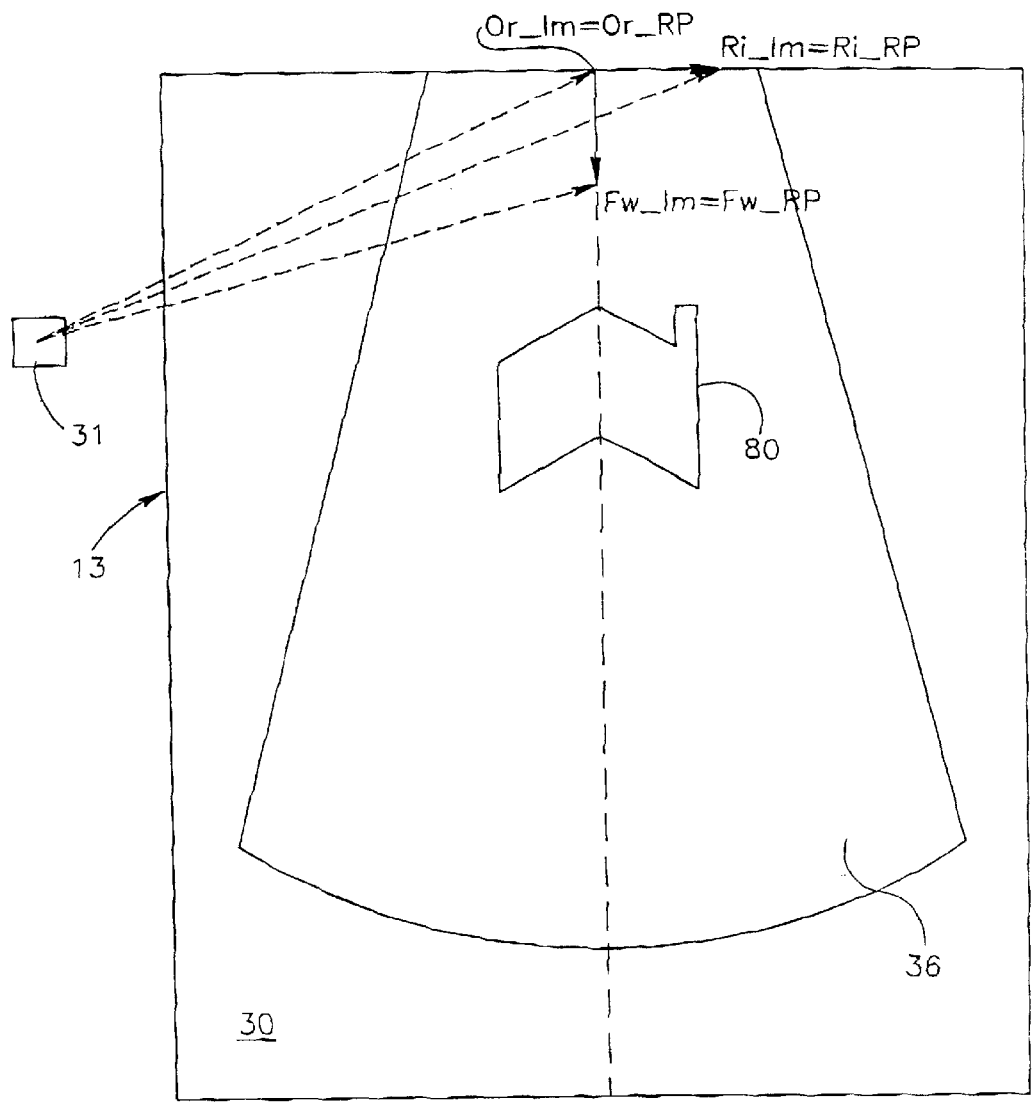
FIG. 9a illustrates the relative position between the three points (non-collinear) that define the image or scanning plane and three points (non-collinear) defining the reference plane with respect to the second position measuring component, as viewed on a visual display, when the image or scanning plane and the reference plane coincide.

FIG. 9a illustrates the display 13 when the ultrasound transducer 3 emits a beam 36 to scan the reference plane 30, such that the origin (Or_Im)of the image or scanning coincides with the origin (Or_RP) of the reference plane 30, as illustrated in FIG. 9a. When this happens the scanning and reference planes are coincident. Therefore the position of the three points determining the scanning plane with respect to the position measuring component 31 attached onto (or being at known position from) the calibration device is:

$Or\_Im,Ref=Or\_RP$ $Ri\_Im,Ref=Ri\_RP$ $Fw\_Im,Ref=Fw\_RP$

The index "Im" refers to the image or scanning plane from the beam 36, the index "Ref" refers to the position measuring component 31, the index "RP" refers to the reference plane 30 with respect to the position measuring component 31 and the index "U" refers to the position measuring component 4 on the ultrasound transducer 3.

Figure 9B:
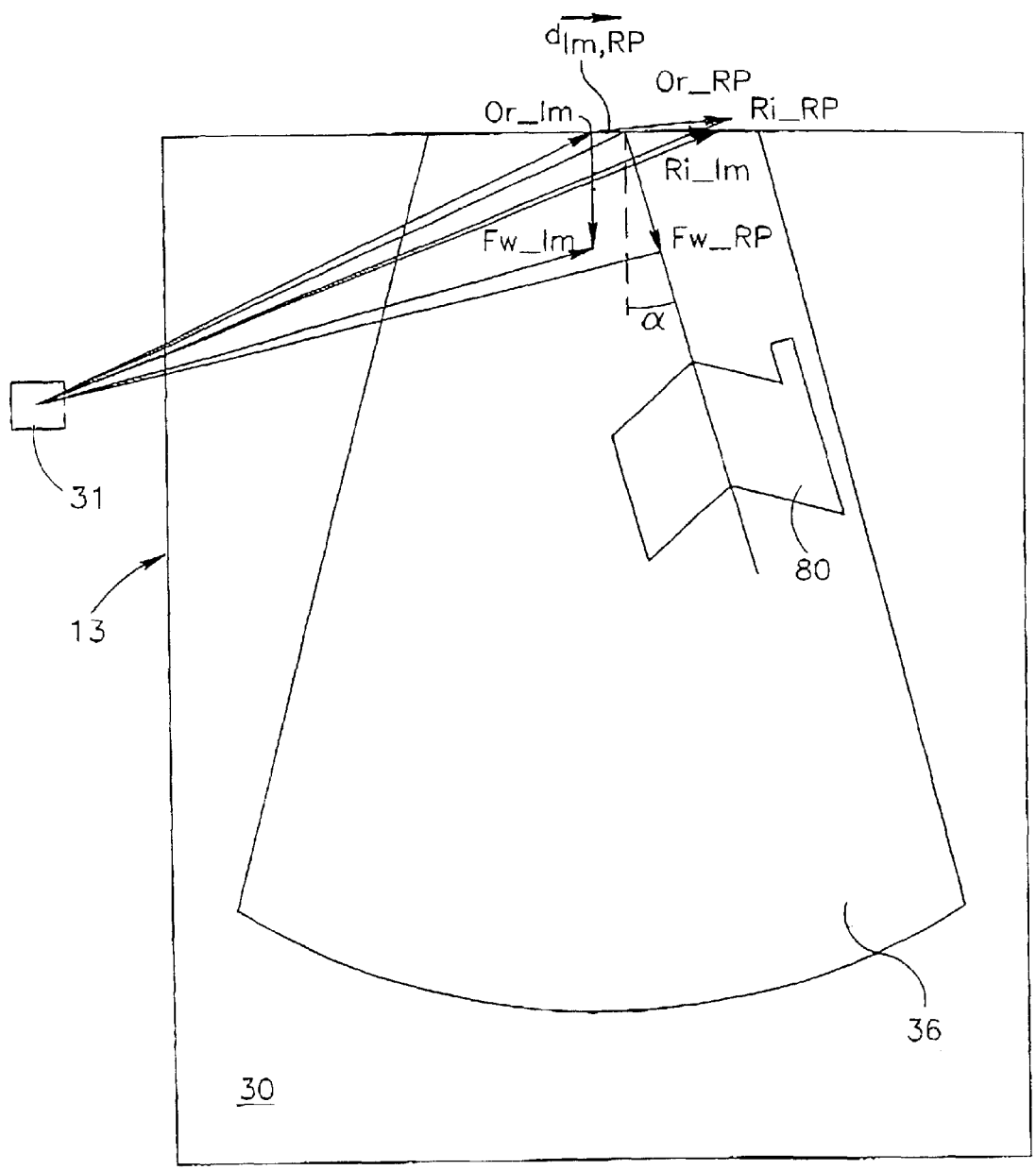
FIG. 9b illustrates the relative position between three points (non-collinear) that define the image or scanning plane and three points (non-collinear) defining the reference plane with respect to the second position measuring component, as viewed on a visual display, when the image or scanning plane is two-dimensionally shifted and rotated with respect to the reference plane, but still coplanar.

FIG. 9b illustrates the display 13 when the ultrasound transducer 3 scans the reference plane 30, such that during the calibration process, the reference plane 30 is two-dimensional shifted, and rotated with respect to the image or scanning plane (from the transducer beam 36). In this case, the computer, such as computer 12 (detailed above), must compensate for shift and two-dimensional rotation of the scanned image with respect to the reference plane 30 by image processing and computer vision tools. In order to calibrate, when the image or scanning plane and the reference plane 30 are coplanar and the cluster 80 (of targets), or part of it, is detected and identified, the image processor 35 (FIGS. 2b –2g) calculates the rotation and two-dimensional vector shift between the two planes (reference 30 and image or scanning): rotation matrix [MIm.RP] and vector shift dIm,RP. The position of the 3 points defining the image plane with respect to the component of the position measuring system attached onto (or being at known position from) the calibration device is then calculated as follows:

$Or\_Im,Ref=Ri\_RP+[MRP.Ref]^T dIm,RP$ $Ri\_Im,Ref=Ri\_RP+[MRP.Ref]^T*(dIm,RP+[MIm.RP]^T*[1,0,0]^T)$ $Fw\_Im,Ref=Fw\_RP+[MRP.Ref]^T*(dIm,RP+[MIm.RP]^T*[0,1,0]^T)$

The computer calculates the location and orientation of the position measuring component 31 related to the calibrating device with respect to the position measuring component 4 attached on the ultrasound transducer 3, the rotation matrix [MU,Ref] and displacement vector dU,ref. This is performed by directly or indirectly measuring the position of each position measuring component 31, 4 with respect to a reference position (as described above).

Therefore, the position of the three points determining the image plane with respect to the transducer attached component of the position measuring system can be calculated as follows:

$Or\_Im,U=[MU.Ref]*(Or\_Im.Ref-dU,Ref)$ $Ri\_Im,U=[MU,Ref]*(Ri\_Im,Ref-dU,Ref)$ $Fw\_Im,U=[MU,Ref]*(Fw\_Im,Ref-dU,Ref)$

This final calculation concludes the algorithm. Alternative mathematical algorithms can be used in order to calculate the position of the scanning beam 36 with respect to the position measuring component 4, attached to the ultrasound transducer 3.

According to still further features of the present invention, the target arrangement in the chamber 20 of the calibrating device (FIG. 2a) enables placing the ultrasound transducer 3 at any position or orientation on the chamber 20, and calculating the position of the scanning plane with respect to the reference plane 30 without any need maneuver the ultrasound transducer 30. One suitable target (target volume) arrangement is illustrated in FIGS. 13, 14, 15a, 15b, 16a, 16a' and 16b.

Figure 13:
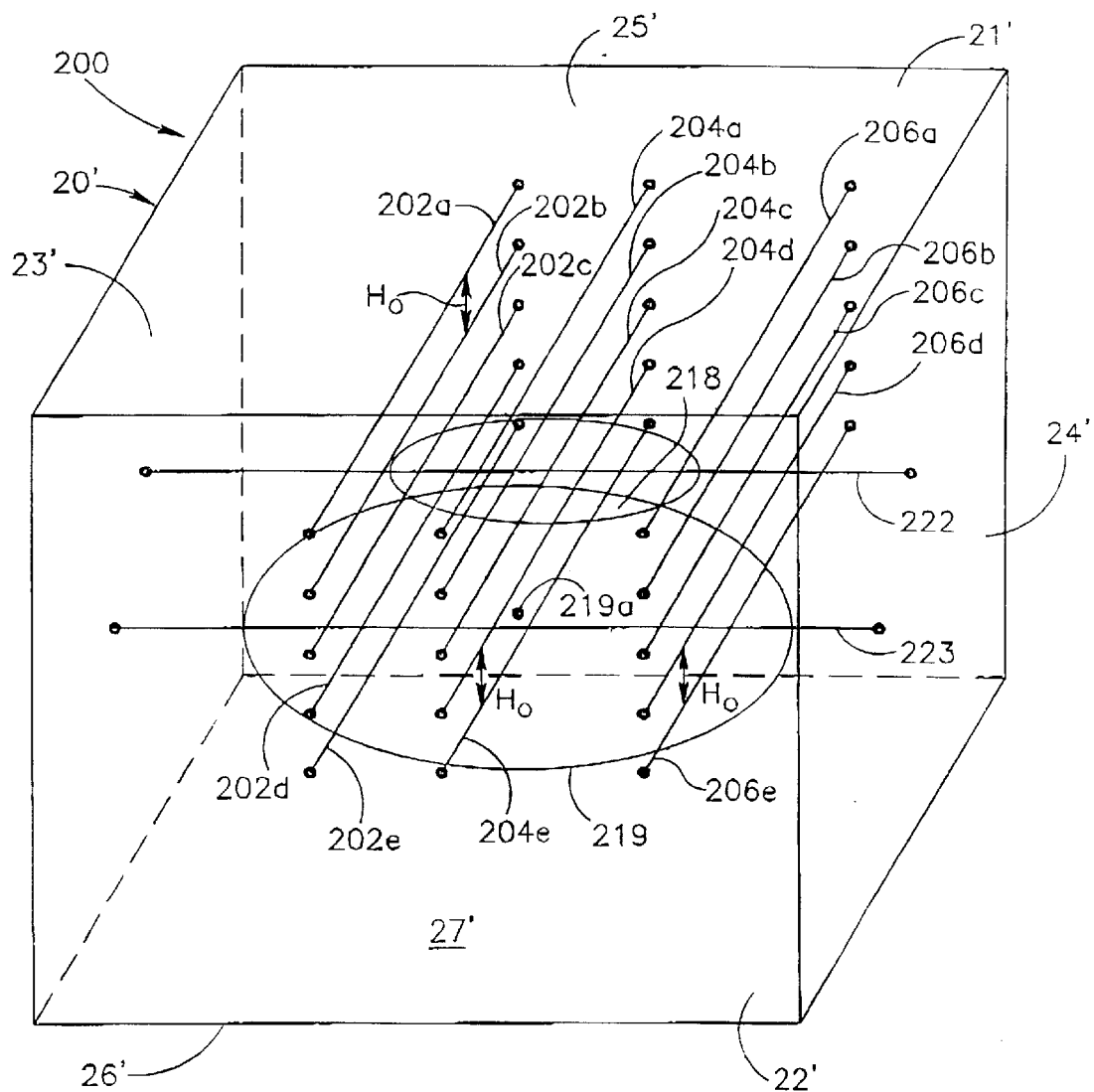
FIG. 13 is a perspective view of a second chamber used in the calibration methods of the present invention.
Figure 14:
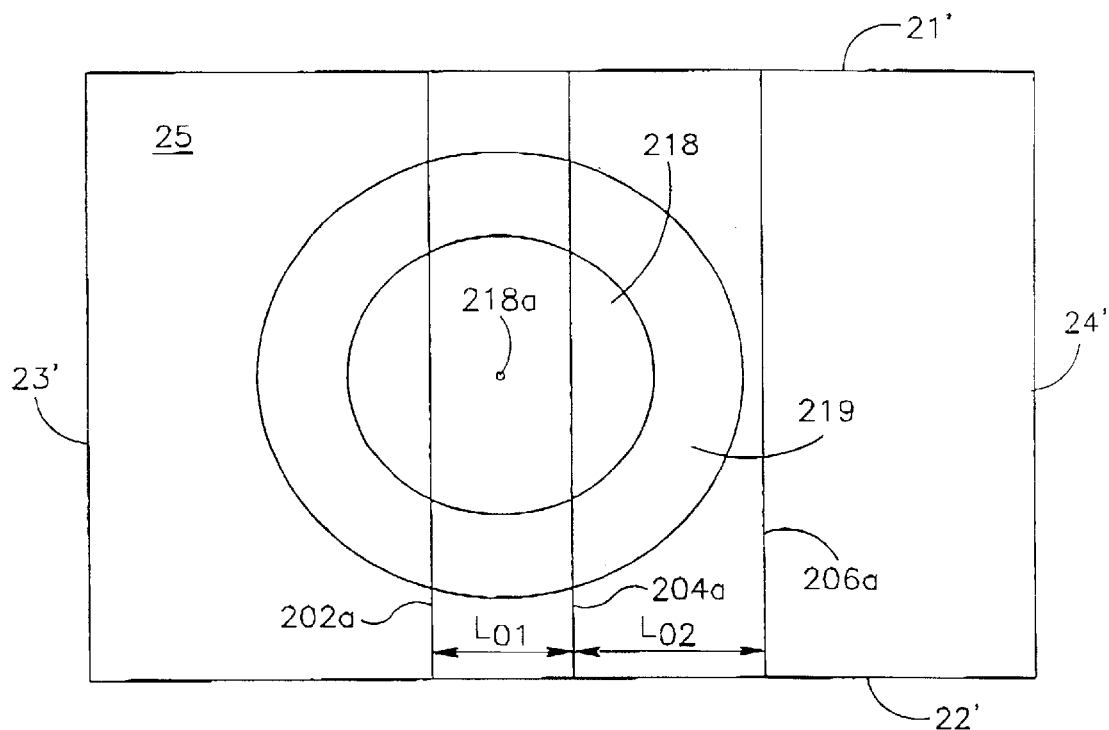
FIG. 14 is a top view of FIG. 13.

FIGS. 13 and 14 show a second calibration apparatus 200. This apparatus 200 includes a chamber 20' similar in construction, materials and function to the chamber 20 of the calibration device above, as shown in detail in FIG. 2a. The chamber 20' has an interior 27' and a series of echogenic elements 202a–202e, 204a–204e, 206a–206e, preferably in columns (in accordance with numbers 202, 204, 206), and substantially parallel to each other, and most preferably parallel to each, attached to first 21' and second 22' lateral walls.

The series of echogenic elements define target clusters or a target volume(s). All echogenic elements are in accordance with those detailed above. The chamber 20' includes a top wall 25' and a bottom wall 26', with all walls similar in construction and materials to their corresponding walls in chamber 20, as detailed above (FIG. 2a).

The echogenic elements in a column, for example echogenic elements 202a–202e are preferably equally spaced, such that $H_o$=1 cm, the distance therebetween. For example, the distance between the first column (formed by echogenic elements 202a–202e) and the second column (formed by echogenic elements 204a–204e) can be expressed as $L_{o1}$=1 cm, and the distance between the second and third column (formed by echogenic elements 206a–206e) can be expressed as $L_{o2}$2 cm.

The chamber 20' also includes at least two concentric circles 218, 219 preferably substantially parallel, and most preferably parallel to the top wall 25' and at different depths, and radaii, respectively. These circles 218, 219 are held in the chamber 20' by supports 222, 223 respectively, attached to the first 23' and second 24' end walls. For example, depths (measured from the top wall 25' ) are 2.5 cm and 3.5 cm, respectively, while diameters $C_{o1}$=2 cm and $C_{o2}$=3 cm respectively. The centers 218a, 219a of these respective circles are positioned equidistant from the first (202a–202e) and second (204a–204e) column of echogenic elements. Within this chamber 20', a reference plane, corresponding to the reference plane 30 detailed above (see FIG. 2a) is defined, such that its origin is the intersection of the line passing through the centers 218a, 219a of the circles 218, 219. The forward point ($FW_{Ref}$) of the reference plane is defined at a distance of 1 unit from the origin ($Or_{Ref}$) in the direction of the center 218a of the circle 218 The right point ($Ri_{Ref}$) is defined at a distance is 1 unit from the origin in the direction perpendicular to the planes defined by columns of targets 202a–202e, 204a–204e, 206a–206e, respectively.

Figure 15A:
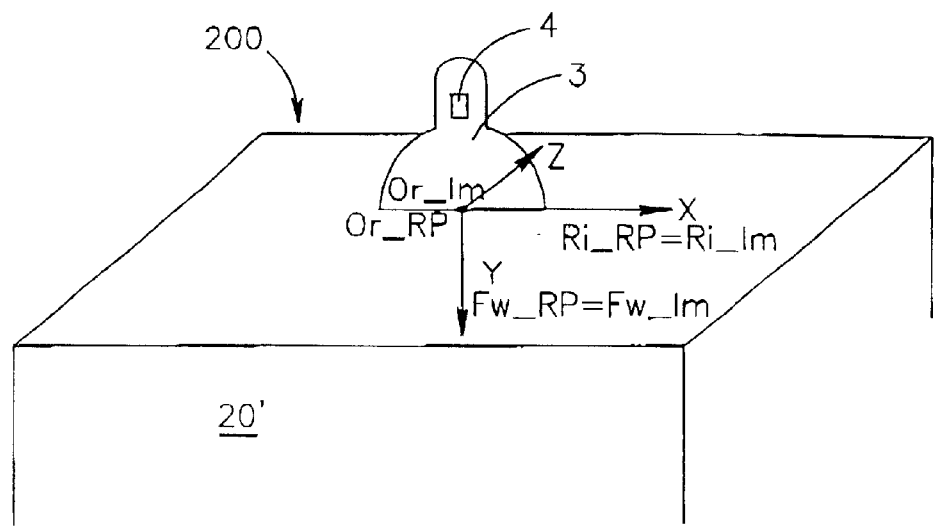
FIGS. 15a and 15b are diagrams useful in understanding the present invention.
Figure 15B:
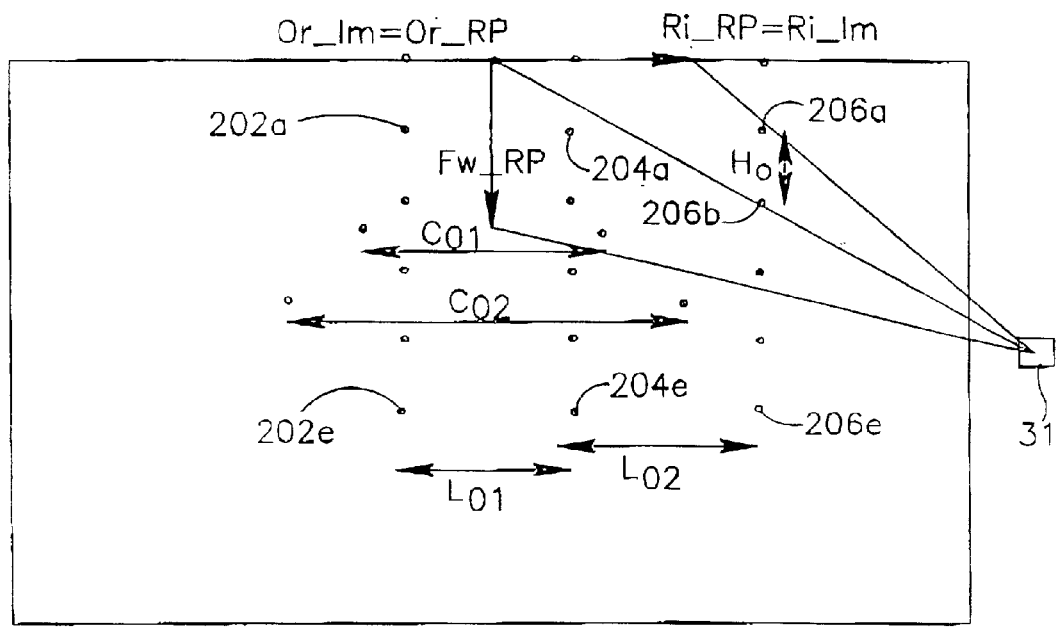

FIG. 15a shows an ultrasound transducer 3, for example from the set ups of FIGS. 2a–2g over the calibration chamber 20' (on the calibration device 200). Specifically, the ultrasound transducer 3 is oriented such that vectors corresponding to the scanning plane Or_Im,Ref, Ri_Im,Ref and Fw,_Im,Ref are equal to corresponding reference plane vectors Or_RP, Ri_RP and Fw_RP. FIG. 15b illustrates the image on the display 13 (FIGS. 1a, 1b) received when the scanning plane is superimposed over the reference plane, as the vectors are equivalent, as in FIG. 15a.

Figure 16A:
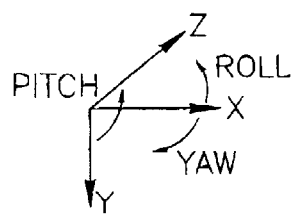
FIGS. 16a, 16a' and 16b are also are diagrams useful in understanding the present invention.
Figure 16A:
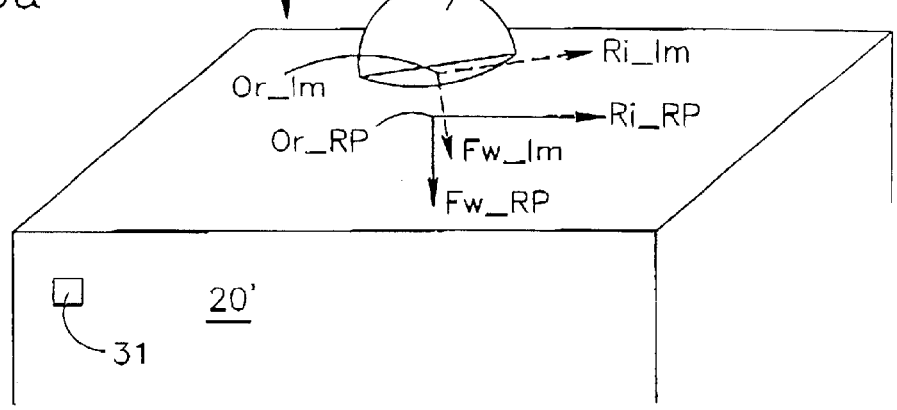
Figure 16B:
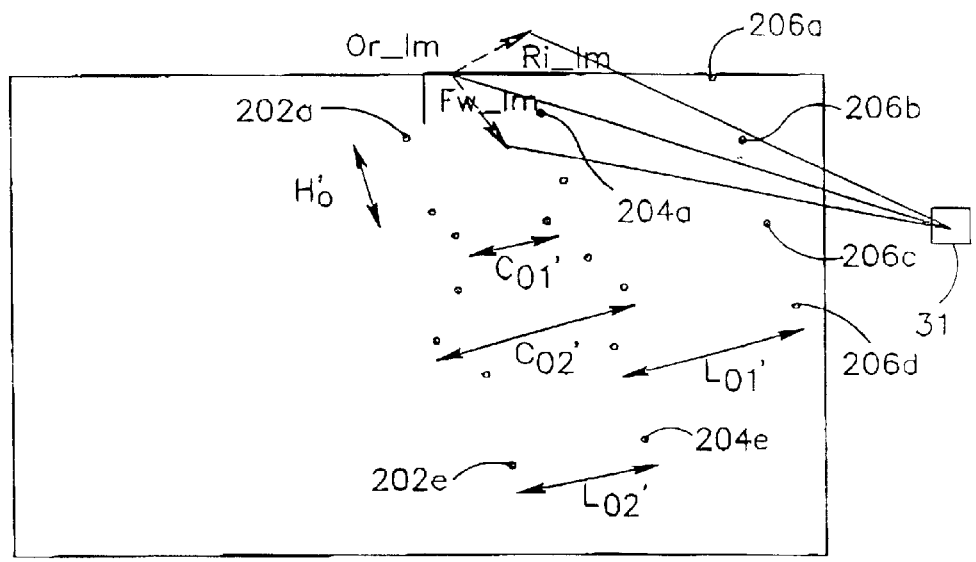

In FIGS. 16a, 16a' and 16b the ultrasound transducer 3 is positioned such that the resultant scanning plane is not superimposed over the reference plane, as in FIGS. 15a and 15b. Rather, the scanning plane is shifted and three-dimensionally rotated with respect to the reference plane 30, such that the scanning plane bisects the reference plane 30 at a bisecting angle.

Referring to FIGS. 16a' and 16b, the distance between the two displayed columns of targets $L+_{o1}$ and $L'_{o2}$ enables the roll to be determined. The distance between the rows of segments $H'_o$ enables determination of the pitch. The angle between columns of segments and the vertical line of the scanning plane (forward, Fw,Im) enables determination of the yaw.

The size of the cords $C'_{o1}$ and $C'_{o2}$ establishes the distance between the origin of the scanning plane and the reference plane. It is employed together with the ratio between the distances of the center of the scanning plane to the lines defined by the column of segments in order to establish the x, z displacement between the reference and scanning planes.

Since the relative position of the scanning plane can be established with respect to the reference plane, it can be established with respect to the position to measuring component 31, that is attached or associated with the calibration chamber 20'. Therefore, the device illustrated enables placing the ultrasound transducer 3 freely over the calibration chamber 20' and calibrating the position measuring component 4 on the ultrasound transducer 3 with respect to the scanning plane, without the need for additional maneuvering of the ultrasound transducer 3.

Figure 17:
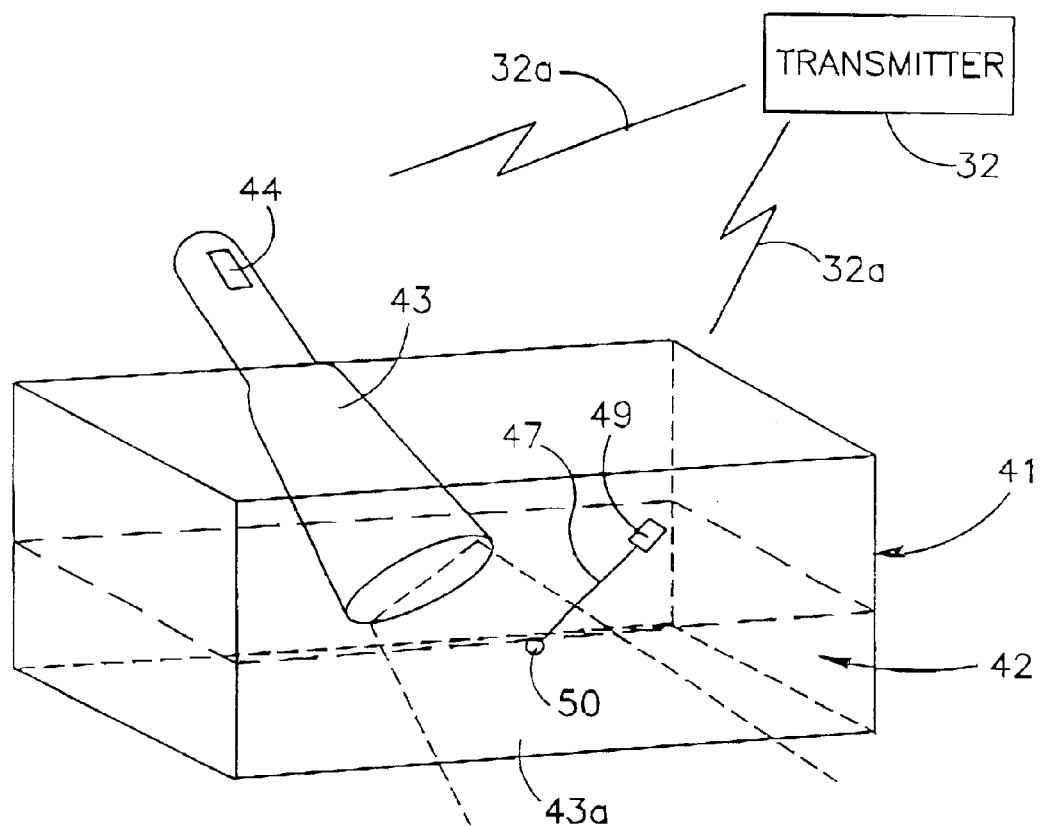
FIG. 17 illustrates an alternative setup for calibrating an ultrasound transducer in accordance with another embodiment of the present invention.
Figure 18:
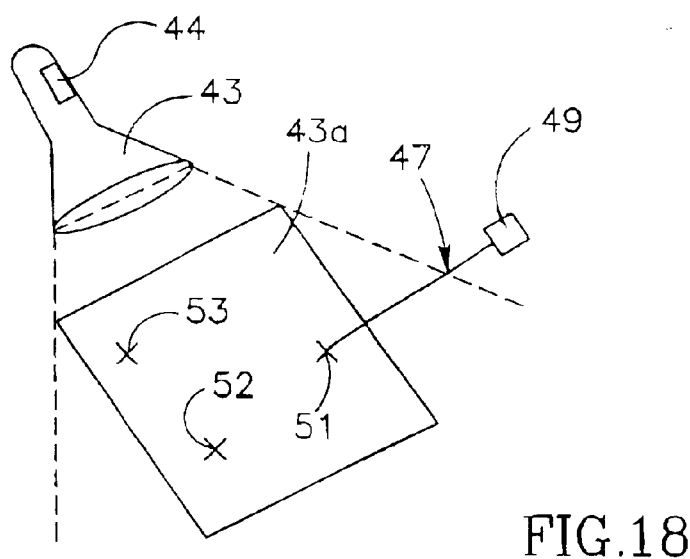
FIG. 18 is a diagram helpful in explaining the operation of the calibration setup of FIG. 17.

FIGS. 17 and 18 illustrate the second embodiment of the present invention. The apparatus used according to the method illustrated in these figures includes a container 41 filled with a liquid 42 whose properties of ultrasound propagation are similar to those of the biological tissue to be scanned. The ultrasound transducer 43 (corresponding to ultrasound transducer 3 detailed in FIGS. 1a, 1b and 2a–2g above), having a position measuring component (detailed above), here a position sensor 44, fixed to it, is immersed in the liquid.

In the methods illustrated in FIGS. 17 and 18, the calibration device is a manipulatable rigid and fixed-length device (further defined as "needle"), such as a biopsy needle 47, having attached a position measuring component (detailed above), here a position sensor 49, that is used for calibrating the location and orientation of the scanning beam plane 43a with respect to the position sensor 44 carried by the ultrasound transducer 43. For this purpose, the needle 47 used for calibrating the ultrasound transducer 43 carries a position measuring component (detailed above), here a position sensor 49, at a fixed, known distance from the tip 50 of the needle.

All systems, apparatus and methods, and variations thereof, relates to the disclosure of FIGS. 2a–2g above, is relevant for this embodiment. For example, the position measuring component 44 attached to the ultrasound transducer 43 to be calibrated to the ultrasound scanning plane 43a, can be a position sensor, a transmitter, a transceiver, reflector, etc. as detailed above. This is the same for the position measuring component 49 attached to the needle 47. The measurement of the relative position between devices is performed either "directly", in accordance with that detailed above, or "indirectly", with the addition of a third position measuring component 32 (detailed above), for example, a transmitter, this third position measuring component 32 acting as a reference point in space, as detailed above.

The needle 47 is manipulated while the ultrasound transducer 43 is operated, to sense at least three points plane defining the transducer scanning plane 43a. Measuring the location and orientation of these at least three non-collinear points, with respect to the position measuring component 44 attached to the ultrasound transducer 43, while measuring their position with respect to the scanning or image plane 43a defines unambiguously the location and orientation of the scanning and image plane 43a with respect to the position measuring component 44 attached on the ultrasound transducer 43.

FIG. 18 illustrates one possible manner in which the needle 47, carrying its position sensor 49, is used for calibrating the location and orientation of the scanning plane 43a of transducer 43 with respect to position sensor 44 on the transducer. Additionally, in this figure, it is illustrated how the needle 47 can be manipulated towards the scanning beam plane 43a in an out-of-plane manner (the needle 47 is not in the plane of the beam) until the tip 50 of the needle 47 touches the scanning plane 43a (by manipulation of the needle 47 by an operator), such that needle tip 50 touches the scanning plane 43a at point 51 (and then at points 52 and 53).

This event is detected by an echo appearing on the screen (display 13, in the system illustrated in FIG. 1). The computer 12 (FIGS. 1a and 1b) registers, at this instant, the position of the sensor 49, and also the position of the sensor 44 on the transducer 43.

The designation of the event can be performed by the operator, upon signaling the computer that the needle 47 is in position (the needle tip touches the scanning plane) when the echo of the needle tip 50 appears on the display 13 (FIGS. 1a and 1b). Alternately, this event is automatically detected from the ultrasound image by image processing tools (image processor 35, as detailed in FIGS. 2b–2g above).

The computer 12 then calculates the position of the position sensor 44 (or other position measuring component) attached to transducer 43 with respect to the position sensor 49 (or other position measuring component) attached to the needle 47 by directly measuring or by indirectly measuring each position sensor 44, 49 with respect to a reference position measuring component, such as position measuring component 32, in space (as described above). Since the position of the needle tip 50 is known with respect to the position sensor 49 attached to the needle 47, it is possible to calculate the position of the needle tip 50 with respect to the position sensor 44 attached to the ultrasound transducer 43. In parallel, the position of the needle tip echo in the image is recorded by image processing tools (in the image processor 35 in FIGS. 2b–2g above), typically in conjunction with the computer 12.

The position of the needle tip echo can be indicated on the display by the operator, such as by clicking a cursor on the echo on the display, with the use of a mouse. Alternately, the coordinates of the needle tip echo are found automatically by the computer.

The foregoing procedure is repeated two (or more) further times in order to precisely locate the tip 50 of needle 47 to detect at least two further non-collinear points in the scanning plane 43a. Since three non-collinear points define a plane, it will be seen that this procedure enables the precise location and orientation of the scanning plane 43a to be determined with respect to the position sensor 44 on the transducer 43.

The ultrasound beam 20, while having a relatively thin transverse thickness, still may not define an ideal zero-thickness plane. For this reason, the above-described calibration process can be repeated after the ultrasound transducer has been turned around 180°, and the average recorded values produced by the two procedures is used in calibrating the transducer during actual clinical procedures.

While the needle 47 can be manipulated by an operator grasping it directly, as detailed above, it can also be manipulated by an automatic or semiautomatic arm, similar to the arm 15, 15' detailed above. This automatic/semiautomatic arm would hold the needle 47 for the above-detailed manipulation.

During the calibration process, ultrasound transducer 43 may be moved freely, and positioned at different locations and orientations, and the tip of the needle 50 is maneuvered to touch the scanning plane 43a in any at least three non-collinear points (for example, points 51, 52, 53). Alternately, during this calibration process, the ultrasound transducer 43 is held still while measuring the at least three-points as described above, and the needle tip 50 is maneuvered to cross the scanning plane 43a in any at least three non-collinear points.

The following algorithm is exemplary for finding the position of the scanning plane 43a with respect to the position measuring component, here the position sensor 44 attached to the ultrasound.

Initially, any plane in space can be defined either by the parametric equation:

$$a^*x + b^*y + c^*z = d \qquad (\text{Eq. 1})$$

where, a, b, c, d are scalars defining the plane and (x, y, z) are the coordinates of points in the plane, or by the vector description:

$$X = W + s^*(V-W) + t^*(U-W) \qquad (\text{Eq. 2})$$

where W, 6, U are the three non-collinear points on the plane, and s, t are scalars.

The position of the needle tip 50 is known and fixed with respect to the position measuring component 49 attached to it vector dnt,Ref. The position of the position measuring component 44 attached on the ultrasound transducer 43 is measured with respect to the position measuring component 49 attached to the needle 47, to determine the vector (dU,Ref) and orientation matrix [Mu.Ref]. Therefore, the position of the needle tip 50 can be calculated with respect to the position measuring component 44 attached to the ultrasound transducer 43:

$$dnt, U = [MU, Ref]^* \{dnt, Ref - Ref\}$$

During the calibration process the needle tip 50 position is therefore calculated, as described above, in at least three non-collinear positions with respect to scanning or image plane 43a as well as with respect to the position measuring component 44 attached to the ultrasound transducer 43.

If the number of measured points is exactly "3", then the equation of the image plane with respect to the position measuring component attached onto the ultrasound is unambiguously defined (employ Equation 1 or 2). If the number of measured points exceeds 3, then because of measuring errors and width of the ultrasound beam the measured points may not necessarily be coplanar, and it is necessary to find the "best matched" plane. One standard criterion to find the best matched plane can be minimizing the square distance of the measured points from the plane. Additional criterions can be employed.

In general, the minimization process is more suited to be performed in connection to Equation 1, i.e. substituting the coordinates of the measured points, $(dnt,U)i$, in Equation 1, and solving the equation with the additional criterion constraints.

The projection of three measured points, e.g., points 51, 52, 53, that are the closest to the "best matched" plane are then found and labeled P1,U, P2U and P3,U (if there are only three measured points, then these are the points themselves). The position of these three points is known with respect to the scanning or image plane 43a (calculated by the image processor 35, above). P1,Im, P2,Im and P3,Im, and therefore the position of the points Or_Im, Ri_Im and Fw_Im (defined as above) can be calculated with respect to these three points in the image as follows:

$$Or\_Im = s1*(P2,Im-P1,Im) + t1*(P3,Im-P1,Im) + P1,Im$$

$$Ri\_Im = s2*(P2,Im-P1,Im) + t2*(P3,Im-P1,Im) + P1,Im$$

$$Fw\_Im = s3*(P2,Im-P1,Im) + t3*(P3,Im-P1,Im) + P1,Im$$

After calculating the scalars s1, t1, s2, t2, s3 and t3 it is possible to calculate the three points defining the image plane with respect to the position measuring component 44 on the ultrasound transducer 43. These points, Or_Im,U, and Ri_Im,U and Fw_Im,U are determined as follows:

$$Or\_Im,U = s1*(P2,U-P1,U) + t1*(P3,U-P1,U) + P1,U$$

$$Ri\_Im,U = s2*(P2,U-P1,U) + t2*(P3,U-P1,U) + P1,U$$

$$Fw\_Im,U = s3$$

$$*(P2,U-P1,U) + t3$$

$$*(P3,U-P1,U) + P1,U$$

While the above algorithm was disclosed, alternate algorithms can be used in order to find the position of the ultrasound image and scanning plane 43a, with respect of the position measuring component 44 attached to the ultrasound transducer 43.

Once the location and orientation of the scanning plane 43a have been determined with respect to the position measuring component 44 on the ultrasound transducer 43, this calibration data will remain the same during the use of that particular transducer 43 until the location of the position sensor 44 on the transducer 43 is changed, whereupon the transducer 43 would have to be re-calibrated.

According to still further features of the present invention, the calibrating method and apparatus of the present invention can be modified accordingly in order to calibrate devices being mounted on some other medical imaging device, such as a CT (Computerized Tomography) or MRI (Magnetic Resonance Imaging). The calibration process is performed as the calibrating device, such as the calibrating device having the chamber 20 detailed in FIG. 2a above, and the targets or target volume(s) (if a device similar to device 200 detailed in FIGS. 13 and 14 is used) are chosen, such as to enable imaging and recognition on the respective imaging device, and also to define at least one reference plane, such as reference plane 30 (e.g., in FIG. 2a above) in accordance with that detailed above. These targets or target volume(s) must be identifiable by the CT or the MRI, respectively. A position measuring component (detailed above) being attached to the calibrating device or at a known position from the reference plane is employed as detailed above. The matching between the scanning plane of the medical imaging device and the reference plane would be found in a suitable manner by either maneuvering the calibrating device or the imaging device. Either the medical imaging device and/or the calibrating device are maneuvered such that when the imaging device scans the calibrating device, the relative position between the imaging plane and the reference plane can be established either by the operator, or under computer control, as detailed above.

Once the relative position between the scanning or image plane and the reference plane is established, the position of the scanning or image plane can also be calculated with respect to the position measuring component, being attached to the calibration device. In addition, the position of the position measuring component, being attached to the calibration device, can be measured with respect to the position measuring component being attached to the imaging device. From the above values obtained, the position of the scanning or image plane can be calculated with respect to the position measuring component being attached to the medical scanning device, as detailed above.

While the invention has been described with respect to preferred embodiments, it will be appreciated that these are set forth merely for purpose of example, and that many modifications of the invention may be made. The preceding description is intended to be exemplary and should not be used to limit the scope of the invention, that should be determined by reference to the following claims.

What is claimed is:

1. A method for calibrating a medical imaging device scanning and imaging plane to a first position measuring component being attached onto said medical imaging device, the method comprising the steps of:

establishing a reference plane, said reference plane at a first location;

arranging a target volume identifiable by the medical imaging device scanning transducer, around said reference plane;

providing a second position measuring component having a known position with respect to said reference plane;

manipulating said medical imaging device scanning transducer to scan said target volume;

determining the position of said scanning plane with respect to said reference plane;

determining the position of said first position measuring component with respect to said second position measuring component; and processing data corresponding to the position of said first position measuring component with respect to said second position measuring component, and data corresponding to the position of said scanning plane with respect to said reference plane in order to calculate the position of said scanning plane with respect to said first position measuring component.

2. The method of claim 1, wherein said step of determining the position of said first position measuring component relative to said second position measuring component, includes directly measuring the position of said first position measuring component relative to second position measuring component.

3. The method of claim 2, wherein said first and second position measuring components are portions of magnetic, acoustic or optical position measuring systems.

4. The method of claim 1, wherein said step of determining the position of said first position measuring component relative to said second position measuring component, includes indirectly measuring the position of said first position measuring component relative to second position measuring component.

5. The method of claim 4, wherein said step of indirectly measuring includes, providing a third position measuring component, and obtaining a first value by measuring the position of said first position measuring component with respect to said third position measuring component;

obtaining a second value by measuring the position of said second position measuring component with respect to said third position measuring component and said second position measuring component;

calculating said position of said first position measuring component relative to said second position measuring component from said first and second values.

6. The method of claim 5, wherein said first, second and third position measuring components are portions of magnetic, acoustic or optical position measuring systems.

7. The method of claim 1, wherein said at least three points are non-collinear.

8. The method of claim 1, wherein said medical imaging device includes an ultrasound medical imaging device.

9. The method of claim 1, wherein the position of said scanning plane with respect to said reference plane is calculated by a computer programmed with image processing means, based on data received upon scanning said target volume.

10. The method of claim 1, wherein said medical imaging device includes a CT medical imaging device.

11. The method of claim 1, wherein said medical imaging device includes a MRI medical imaging device.

* * * * *